United States Patent
Fengler et al.

(10) Patent No.: US 10,779,734 B2
(45) Date of Patent: Sep. 22, 2020

(54) IMAGING SYSTEM FOR COMBINE FULL-COLOR REFLECTANCE AND NEAR-INFRARED IMAGING

(71) Applicant: Stryker European Operations Limited, Carrigtwohill (IE)

(72) Inventors: John Fengler, North Vancouver (CA); Paul R. Westwick, Vancouver (CA); Aurther E. Bailey, North Vancouver (CA); Paul Cottle, Vancouver (CA)

(73) Assignee: Stryker European Operations Limited, Carrigtwohill (IE)

( * ) Notice: Subject to any disclaimer, the term of this patent is extended or adjusted under 35 U.S.C. 154(b) by 0 days.

(21) Appl. No.: 15/584,405

(22) Filed: May 2, 2017

(65) Prior Publication Data
US 2017/0273567 A1 Sep. 28, 2017

Related U.S. Application Data

(63) Continuation of application No. 14/873,842, filed on Oct. 2, 2015, now Pat. No. 9,642,532, which is a
(Continued)

(51) Int. Cl.
*A61B 5/00* (2006.01)
*A61B 1/00* (2006.01)
(Continued)

(52) U.S. Cl.
CPC .......... *A61B 5/0086* (2013.01); *A61B 1/0005* (2013.01); *A61B 1/00045* (2013.01);
(Continued)

(58) Field of Classification Search
None
See application file for complete search history.

(56) References Cited

U.S. PATENT DOCUMENTS

| 1,290,744 A | 1/1919 | Hollander |
| 2,453,336 A | 11/1948 | Orser |

(Continued)

FOREIGN PATENT DOCUMENTS

| CN | 101726980 A | 6/2010 |
| CN | 101828139 A | 9/2010 |

(Continued)

OTHER PUBLICATIONS

US 6,692,429 B1, 02/2004, Imaizumi et al. (withdrawn)
(Continued)

*Primary Examiner* — David N Werner
(74) *Attorney, Agent, or Firm* — Morrison & Foerster LLP

(57) ABSTRACT

An imaging system for acquisition of NIR and full-color images includes a light source providing visible light and NIR light to an area under observation, such as living tissue, a camera having one or more image sensors configured to separately detect blue reflectance light, green reflectance light, and combined red reflectance light/detected NIR light returned from the area under observation. A controller in signal communication with the light source and the camera is configured to control the light source to continuously illuminate area under observation with temporally continuous blue/green illumination light and with red illumination light and NIR excitation light. At least one of the red illumination light and NIR excitation light are switched on and off periodically in synchronism with the acquisition of red and NIR light images in the camera.

11 Claims, 9 Drawing Sheets

Related U.S. Application Data continuation of application No. 12/933,512, filed as application No. PCT/US2009/037506 on Mar. 18, 2009, now Pat. No. 9,173,554.

(60) Provisional application No. 61/037,514, filed on Mar. 18, 2008.

(51) Int. Cl.
    *A61B 1/04* (2006.01)
    *H04N 5/33* (2006.01)
    *A61B 1/045* (2006.01)
    *A61B 1/06* (2006.01)
    *G02B 27/10* (2006.01)

(52) U.S. Cl.
    CPC .......... *A61B 1/00186* (2013.01); *A61B 1/04* (2013.01); *A61B 1/042* (2013.01); *A61B 1/043* (2013.01); *A61B 1/045* (2013.01); *A61B 1/0638* (2013.01); *A61B 1/0646* (2013.01); *A61B 5/0062* (2013.01); *A61B 5/0071* (2013.01); *A61B 5/7425* (2013.01); *G02B 27/1013* (2013.01); *H04N 5/33* (2013.01); *H04N 5/332* (2013.01); *A61B 1/00009* (2013.01); *A61B 1/00043* (2013.01); *A61B 1/00163* (2013.01); *A61B 1/06* (2013.01); *A61B 1/0669* (2013.01); *A61B 5/0075* (2013.01); *A61B 5/418* (2013.01); *G06T 2207/10048* (2013.01)

(56) References Cited

U.S. PATENT DOCUMENTS

| | | |
|---|---|---|
| 2,857,523 A | 10/1958 | Corso |
| 3,215,029 A | 11/1965 | Woodcock |
| 3,582,178 A | 6/1971 | Boughton et al. |
| 3,671,098 A | 6/1972 | Rotter |
| 3,749,494 A | 7/1973 | Hodges |
| 3,790,248 A | 2/1974 | Kellow |
| 3,931,593 A | 1/1976 | Marshall |
| 3,970,373 A | 7/1976 | Pledger |
| 3,971,068 A | 7/1976 | Gerhardt et al. |
| 4,037,866 A | 7/1977 | Price |
| 4,066,330 A | 1/1978 | Jones |
| 4,115,812 A | 9/1978 | Akatsu |
| 4,149,190 A | 4/1979 | Wessler et al. |
| 4,158,504 A | 6/1979 | de Ponteves et al. |
| 4,200,801 A | 4/1980 | Schuresko |
| 4,260,217 A | 4/1981 | Traeger et al. |
| 4,318,395 A | 3/1982 | Tawara |
| 4,355,325 A | 10/1982 | Nakamura et al. |
| 4,378,571 A | 3/1983 | Handy |
| 4,449,535 A | 5/1984 | Renault |
| 4,471,766 A | 9/1984 | Terayama |
| 4,532,918 A | 8/1985 | Wheeler |
| 4,556,057 A | 12/1985 | Hiruma et al. |
| 4,575,632 A | 3/1986 | Lange |
| 4,597,630 A | 7/1986 | Brandstetter et al. |
| 4,611,888 A | 9/1986 | Prenovitz et al. |
| 4,638,365 A | 1/1987 | Kato |
| 4,656,508 A | 4/1987 | Yokota |
| 4,660,982 A | 4/1987 | Okada |
| 4,688,905 A | 8/1987 | Okamura |
| 4,717,952 A | 1/1988 | Kohayakawa et al. |
| 4,742,388 A | 5/1988 | Cooper et al. |
| 4,768,513 A | 9/1988 | Suzuki |
| 4,786,813 A | 11/1988 | Svanberg et al. |
| 4,799,104 A | 1/1989 | Hosoya et al. |
| 4,806,005 A | 2/1989 | Schneider et al. |
| 4,821,117 A | 4/1989 | Sekiguchi |
| 4,837,625 A | 6/1989 | Douziech et al. |
| 4,852,985 A | 8/1989 | Fujihara et al. |
| 4,856,495 A | 8/1989 | Tohjoh et al. |
| 4,885,634 A | 12/1989 | Yabe |
| 4,895,145 A | 1/1990 | Joffe et al. |
| 4,930,516 A | 6/1990 | Alfano et al. |
| 4,930,883 A | 6/1990 | Salzman |
| 4,951,135 A | 8/1990 | Sasagawa et al. |
| 4,953,539 A | 9/1990 | Nakamura et al. |
| 4,954,897 A | 9/1990 | Ejima et al. |
| 4,974,936 A | 12/1990 | Ams et al. |
| 5,001,556 A | 3/1991 | Nakamura et al. |
| 5,007,408 A | 4/1991 | Ieoka |
| 5,028,128 A | 7/1991 | Onuki |
| 5,034,888 A | 7/1991 | Uehara et al. |
| 5,041,852 A | 8/1991 | Misawa et al. |
| 5,115,308 A | 5/1992 | Onuki |
| 5,121,220 A | 6/1992 | Nakamoto |
| 5,128,803 A | 7/1992 | Sprafke |
| 5,132,837 A | 7/1992 | Kitajima |
| 5,134,662 A | 7/1992 | Bacus et al. |
| 5,159,398 A | 10/1992 | Maekewa et al. |
| 5,165,079 A | 11/1992 | Schulz-Hennig |
| 5,205,280 A | 4/1993 | Dennison, Jr. et al. |
| 5,208,651 A | 5/1993 | Buican |
| 5,214,503 A | 5/1993 | Chiu et al. |
| 5,225,883 A | 7/1993 | Carter et al. |
| 5,255,087 A | 10/1993 | Nakamura et al. |
| 5,278,642 A | 1/1994 | Danna et al. |
| 5,282,082 A | 1/1994 | Espie et al. |
| 5,295,017 A | 3/1994 | Brown |
| RE34,622 E | 5/1994 | Ledley |
| 5,365,057 A | 11/1994 | Morley et al. |
| 5,371,355 A | 12/1994 | Wodecki |
| 5,377,686 A | 1/1995 | O'Rourke et al. |
| 5,379,756 A | 1/1995 | Pileski et al. |
| 5,408,263 A | 4/1995 | Kikuchi et al. |
| 5,410,363 A | 4/1995 | Capen et al. |
| 5,419,323 A | 5/1995 | Kittrell et al. |
| 5,420,628 A | 5/1995 | Poulsen et al. |
| 5,421,337 A | 6/1995 | Richards-Kortum et al. |
| 5,424,841 A | 6/1995 | Van Gelder et al. |
| 5,426,530 A | 6/1995 | Copenhaver et al. |
| 5,430,476 A | 7/1995 | Häfele et al. |
| 5,481,401 A | 1/1996 | Kita et al. |
| 5,485,203 A | 1/1996 | Nakamura et al. |
| 5,490,015 A | 2/1996 | Umeyama et al. |
| 5,507,287 A | 4/1996 | Palcic et al. |
| 5,515,449 A | 5/1996 | Tsuruoka et al. |
| 5,535,052 A | 7/1996 | Jörgens |
| 5,536,236 A | 7/1996 | Yabe et al. |
| 5,557,451 A | 9/1996 | Copenhaver et al. |
| 5,585,846 A | 12/1996 | Kim |
| 5,590,660 A | 1/1997 | MacAulay et al. |
| 5,596,654 A | 1/1997 | Tanaka |
| 5,646,680 A | 7/1997 | Yajima |
| 5,647,368 A | 7/1997 | Zeng et al. |
| 5,647,840 A | 7/1997 | D'Amelio et al. |
| 5,667,472 A | 9/1997 | Finn et al. |
| 5,677,724 A | 10/1997 | Takizawa et al. |
| 5,682,567 A | 10/1997 | Spruck et al. |
| 5,689,354 A | 11/1997 | Orino |
| 5,695,049 A | 12/1997 | Bauman |
| 5,697,373 A | 12/1997 | Richards-Kortum et al. |
| 5,713,364 A | 2/1998 | DeBaryshe et al. |
| 5,729,382 A | 3/1998 | Morita et al. |
| 5,749,830 A | 5/1998 | Kaneko et al. |
| 5,769,792 A | 6/1998 | Palcic et al. |
| 5,772,355 A | 6/1998 | Ross et al. |
| 5,772,580 A | 6/1998 | Utsui et al. |
| 5,827,190 A | 10/1998 | Palcic et al. |
| 5,833,617 A | 11/1998 | Hayashi |
| 5,838,001 A | 11/1998 | Minakuchi et al. |
| 5,840,017 A | 11/1998 | Furuswaba et al. |
| 5,852,498 A | 12/1998 | Youvan et al. |
| 5,891,016 A | 4/1999 | Utsui et al. |
| 5,897,269 A | 4/1999 | Ross et al. |
| 5,971,918 A | 10/1999 | Zanger |
| 5,973,315 A | 10/1999 | Saldana et al. |
| 5,984,861 A | 11/1999 | Crowley |
| 5,986,271 A | 11/1999 | Lazarev et al. |
| 5,986,642 A | 11/1999 | Ueda et al. |

(56) References Cited

U.S. PATENT DOCUMENTS

| | | |
|---|---|---|
| 5,990,996 A | 11/1999 | Sharp |
| 5,999,240 A | 12/1999 | Sharp et al. |
| 6,002,137 A | 12/1999 | Hayashi |
| 6,004,263 A | 12/1999 | Nakaichi et al. |
| 6,008,889 A | 12/1999 | Zeng et al. |
| 6,021,344 A | 2/2000 | Lui et al. |
| 6,028,622 A | 2/2000 | Suzuki |
| 6,030,339 A | 2/2000 | Tatsuno et al. |
| 6,059,719 A | 5/2000 | Yamamoto et al. |
| 6,059,720 A | 5/2000 | Furusawa et al. |
| 6,061,591 A | 5/2000 | Freitag et al. |
| 6,069,689 A | 5/2000 | Zeng et al. |
| 6,070,096 A | 5/2000 | Hayashi |
| 6,095,982 A | 8/2000 | Richards-Kortum et al. |
| 6,099,466 A | 8/2000 | Sano et al. |
| 6,110,106 A | 8/2000 | MacKinnon et al. |
| 6,120,435 A | 9/2000 | Eino |
| 6,147,705 A | 11/2000 | Krauter et al. |
| 6,148,227 A | 11/2000 | Wagnières et al. |
| 6,161,035 A | 12/2000 | Furusawa |
| 6,181,414 B1 | 1/2001 | Raz et al. |
| 6,192,267 B1 | 2/2001 | Scherninski et al. |
| 6,212,425 B1 | 4/2001 | Irion et al. |
| 6,226,126 B1 | 5/2001 | Conemac |
| 6,258,576 B1 | 7/2001 | Richards-Kortum et al. |
| D446,524 S | 8/2001 | Bontly et al. |
| 6,280,378 B1 | 8/2001 | Kazuhiro et al. |
| 6,293,911 B1 | 9/2001 | Imaizumi et al. |
| 6,315,712 B1 | 11/2001 | Rovegno |
| 6,332,092 B1 | 12/2001 | Deckert et al. |
| 6,364,829 B1 | 4/2002 | Fulghum |
| 6,364,831 B1 | 4/2002 | Crowley |
| D456,809 S | 5/2002 | Schieffers |
| 6,419,628 B1 | 7/2002 | Rudischhauser et al. |
| 6,422,994 B1 | 7/2002 | Kaneko et al. |
| 6,462,770 B1 | 10/2002 | Cline et al. |
| 6,510,338 B1 | 1/2003 | Irion et al. |
| 6,526,213 B1 | 2/2003 | Ilenda et al. |
| 6,529,239 B1 | 3/2003 | Dyck et al. |
| 6,529,768 B1 | 3/2003 | Hakamata |
| 6,537,211 B1 | 3/2003 | Wang et al. |
| 6,544,102 B2 | 4/2003 | Schäfer et al. |
| 6,571,119 B2 | 5/2003 | Hayashi |
| 6,596,996 B1 | 7/2003 | Stone et al. |
| 6,603,552 B1 | 8/2003 | Cline et al. |
| 6,639,664 B2 | 10/2003 | Haan et al. |
| 6,652,452 B1 | 11/2003 | Seifert et al. |
| 6,750,971 B2 | 6/2004 | Overbeck et al. |
| 6,772,003 B2 | 8/2004 | Kaneko et al. |
| 6,773,392 B2 | 8/2004 | Kikuchi et al. |
| 6,786,865 B2 | 9/2004 | Dhindsa |
| 6,821,245 B2 | 11/2004 | Cline et al. |
| 6,826,424 B1 | 11/2004 | Zeng et al. |
| 6,898,458 B2 | 5/2005 | Zeng et al. |
| 6,899,675 B2 | 5/2005 | Cline et al. |
| 6,922,583 B1 | 7/2005 | Perelman et al. |
| 6,958,862 B1 | 10/2005 | Joseph |
| 6,960,165 B2 | 11/2005 | Ueno et al. |
| 7,043,291 B2 | 5/2006 | Sendai |
| D524,985 S | 7/2006 | Lukan et al. |
| D524,987 S | 7/2006 | Lukan et al. |
| 7,150,552 B2 | 12/2006 | Weidel |
| 7,179,222 B2 | 2/2007 | Imaizumi et al. |
| 7,235,045 B2 | 6/2007 | Wang et al. |
| 7,236,815 B2 | 6/2007 | Richards-Kortum et al. |
| 7,253,894 B2 | 8/2007 | Zeng et al. |
| 7,324,674 B2 | 1/2008 | Ozawa et al. |
| 7,333,270 B1 | 2/2008 | Pochapsky et al. |
| 7,341,557 B2 | 3/2008 | Cline et al. |
| 7,385,772 B2 | 6/2008 | Forkey et al. |
| 7,420,151 B2 | 9/2008 | Fengler et al. |
| 7,479,990 B2 | 1/2009 | Imaizumi et al. |
| D599,799 S | 9/2009 | Di Bari et al. |
| D603,408 S | 11/2009 | Fitch |
| D606,544 S | 12/2009 | Di Bari et al. |
| 7,697,975 B2 | 4/2010 | Zeng |
| 7,704,206 B2 | 4/2010 | Suzuki et al. |
| 7,722,534 B2 | 5/2010 | Cline et al. |
| 7,777,191 B2 | 8/2010 | Olcott et al. |
| 7,798,955 B2 | 9/2010 | Ishihara et al. |
| 7,811,229 B2 | 10/2010 | Sugimoto |
| 7,928,352 B2 | 4/2011 | Toda |
| 8,035,067 B2 | 10/2011 | Toda |
| D653,811 S | 2/2012 | BenZion |
| 8,140,147 B2 | 3/2012 | Maynard et al. |
| 8,285,015 B2 | 10/2012 | Demos |
| 8,337,400 B2 | 12/2012 | Mizuyoshi |
| 8,361,775 B2 | 1/2013 | Flower |
| D677,258 S | 3/2013 | Mistkawi |
| 8,408,269 B2 | 4/2013 | Fengler et al. |
| 8,408,772 B2 | 4/2013 | Li |
| D682,277 S | 5/2013 | Tasselli et al. |
| 8,448,867 B2 | 5/2013 | Liu et al. |
| 8,473,035 B2 | 6/2013 | Frangioni |
| 8,498,695 B2 | 7/2013 | Westwick et al. |
| D692,004 S | 10/2013 | Man |
| 8,630,698 B2 | 1/2014 | Fengler et al. |
| 8,721,532 B2 | 5/2014 | Takei et al. |
| 8,736,748 B2 | 5/2014 | Takita |
| 8,759,243 B2 | 6/2014 | Coffy et al. |
| 8,773,756 B2 | 7/2014 | Tesar et al. |
| 8,790,253 B2 | 7/2014 | Sunagawa et al. |
| 8,830,339 B2 | 9/2014 | Velarde et al. |
| D719,574 S | 12/2014 | Alegiani et al. |
| 8,961,403 B2 | 2/2015 | Cline et al. |
| D723,563 S | 3/2015 | Alegiani |
| 8,979,301 B2 | 3/2015 | Moore |
| D726,186 S | 4/2015 | Jenkins et al. |
| D734,339 S | 7/2015 | Zhou et al. |
| 9,125,552 B2 | 9/2015 | Dunki-Jacobs et al. |
| 9,143,746 B2 | 9/2015 | Westwick et al. |
| 9,173,554 B2 | 11/2015 | Fengler et al. |
| 9,282,305 B2 | 3/2016 | Kikuchi |
| 9,294,691 B2 | 3/2016 | Ooki |
| 9,295,392 B2 | 3/2016 | Douplik et al. |
| 9,386,909 B2 | 7/2016 | Fengler et al. |
| 9,435,496 B2 | 9/2016 | Moore |
| 9,577,012 B2 | 2/2017 | Ooki |
| 9,642,532 B2 | 5/2017 | Fengler et al. |
| D791,137 S | 7/2017 | Wang et al. |
| 9,814,378 B2 | 11/2017 | Moore |
| D815,928 S | 4/2018 | Rummel et al. |
| D826,234 S | 8/2018 | Zhou et al. |
| D835,284 S | 12/2018 | Barker et al. |
| D835,285 S | 12/2018 | Barker et al. |
| 2001/0016679 A1 | 8/2001 | Futatsugi et al. |
| 2001/0028458 A1 | 10/2001 | Xiao |
| 2001/0049473 A1 | 12/2001 | Hayashi |
| 2002/0013937 A1 | 1/2002 | Ostanevich et al. |
| 2002/0016533 A1 | 2/2002 | Marchitto et al. |
| 2002/0021355 A1 | 2/2002 | Utsui et al. |
| 2002/0035330 A1 | 3/2002 | Cline et al. |
| 2002/0076480 A1 | 6/2002 | Hsieh et al. |
| 2002/0138008 A1 | 9/2002 | Tsujita et al. |
| 2002/0143243 A1 | 10/2002 | Geordakoudi et al. |
| 2002/0148902 A1 | 10/2002 | Schlieffers |
| 2002/0155619 A1 | 10/2002 | Kurihara et al. |
| 2002/0156380 A1 | 10/2002 | Feld et al. |
| 2002/0161282 A1 | 10/2002 | Fulghum |
| 2002/0161283 A1 | 10/2002 | Sendai |
| 2002/0161284 A1 | 10/2002 | Tanaka |
| 2002/0168096 A1 | 11/2002 | Hakamata et al. |
| 2002/0175993 A1 | 11/2002 | Ueno et al. |
| 2002/0177778 A1 | 11/2002 | Averback et al. |
| 2002/0186478 A1 | 12/2002 | Watanabe et al. |
| 2002/0196335 A1 | 12/2002 | Ozawa |
| 2003/0002036 A1 | 1/2003 | Haan et al. |
| 2003/0042493 A1 | 3/2003 | Kazakevich |
| 2003/0080193 A1 | 5/2003 | Ryan et al. |
| 2003/0117491 A1 | 6/2003 | Avni et al. |
| 2003/0135092 A1 | 7/2003 | Cline et al. |
| 2003/0153811 A1 | 8/2003 | Muckner |
| 2003/0191368 A1 | 10/2003 | Wang et al. |
| 2003/0229270 A1 | 12/2003 | Suzuki et al. |

(56) References Cited

U.S. PATENT DOCUMENTS

| | | |
|---|---|---|
| 2004/0006276 A1 | 1/2004 | Demos et al. |
| 2004/0010183 A1 | 1/2004 | Dhindsa |
| 2004/0020990 A1 | 2/2004 | Haven et al. |
| 2004/0021859 A1 | 2/2004 | Cunningham |
| 2004/0037454 A1 | 2/2004 | Ozawa et al. |
| 2004/0044275 A1 | 3/2004 | Hakamata |
| 2004/0046865 A1 | 3/2004 | Ueno et al. |
| 2004/0133073 A1 | 7/2004 | Berci et al. |
| 2004/0134990 A1 | 7/2004 | Fitch et al. |
| 2004/0143162 A1 | 7/2004 | Krattiger et al. |
| 2004/0148141 A1 | 7/2004 | Tsujita et al. |
| 2004/0149998 A1 | 8/2004 | Henson et al. |
| 2004/0156124 A1 | 8/2004 | Okada |
| 2004/0186351 A1 | 9/2004 | Imaizumi et al. |
| 2004/0218115 A1 | 11/2004 | Kawana et al. |
| 2004/0225222 A1* | 11/2004 | Zeng ............ A61B 1/043 600/476 |
| 2004/0245350 A1 | 12/2004 | Zeng |
| 2004/0263643 A1 | 12/2004 | Imaizumi et al. |
| 2005/0027166 A1 | 2/2005 | Matsumoto et al. |
| 2005/0096505 A1 | 5/2005 | Imaizumi et al. |
| 2005/0140270 A1 | 6/2005 | Henson et al. |
| 2005/0143627 A1 | 6/2005 | Cline et al. |
| 2005/0154319 A1 | 7/2005 | Cline et al. |
| 2005/0171440 A1 | 8/2005 | Maki et al. |
| 2005/0182291 A1 | 8/2005 | Hirata |
| 2005/0182321 A1 | 8/2005 | Frangioni |
| 2005/0203421 A1 | 9/2005 | Zeng et al. |
| 2005/0225656 A1* | 10/2005 | Ihama ............ H04N 9/045 348/272 |
| 2005/0256373 A1 | 11/2005 | Bar-Or et al. |
| 2005/0273011 A1 | 12/2005 | Hattery et al. |
| 2005/0280783 A1 | 12/2005 | Yamasaki et al. |
| 2005/0288593 A1 | 12/2005 | Geordakoudi et al. |
| 2006/0002141 A1 | 1/2006 | Ouderkirk et al. |
| 2006/0004292 A1 | 1/2006 | Beylin |
| 2006/0017913 A1 | 1/2006 | Kawamata et al. |
| 2006/0089554 A1 | 4/2006 | Ishihara et al. |
| 2006/0094109 A1 | 5/2006 | Trainer |
| 2006/0146322 A1 | 7/2006 | Komachi et al. |
| 2006/0149133 A1 | 7/2006 | Sugimoto et al. |
| 2006/0155166 A1 | 7/2006 | Takahashi et al. |
| 2006/0211915 A1 | 9/2006 | Takeuchi et al. |
| 2006/0215406 A1 | 9/2006 | Thrailkill |
| 2006/0217594 A1 | 9/2006 | Ferguson |
| 2006/0241496 A1 | 10/2006 | Fengler et al. |
| 2006/0247537 A1 | 11/2006 | Matsumoto |
| 2006/0250696 A1 | 11/2006 | McGuire |
| 2006/0258910 A1 | 11/2006 | Stefanchik et al. |
| 2007/0041195 A1 | 2/2007 | Chen |
| 2007/0091634 A1 | 4/2007 | Sakurada |
| 2007/0177152 A1 | 8/2007 | Tearney et al. |
| 2007/0203413 A1 | 8/2007 | Frangioni |
| 2007/0213593 A1 | 9/2007 | Nakaoka |
| 2007/0229309 A1 | 10/2007 | Tomita et al. |
| 2008/0021274 A1 | 1/2008 | Bayer et al. |
| 2008/0024868 A1 | 1/2008 | Okamura |
| 2008/0027280 A1 | 1/2008 | Fengler et al. |
| 2008/0039697 A1 | 2/2008 | Morishita |
| 2008/0074752 A1 | 3/2008 | Chaves et al. |
| 2008/0177140 A1 | 7/2008 | Cline et al. |
| 2008/0208006 A1 | 8/2008 | Farr |
| 2008/0217411 A1 | 9/2008 | Ledwith et al. |
| 2008/0246920 A1 | 10/2008 | Buczek et al. |
| 2009/0012361 A1 | 1/2009 | MacKinnon et al. |
| 2009/0021739 A1 | 1/2009 | Tsujita et al. |
| 2009/0036734 A1 | 2/2009 | Dunki-Jacobs et al. |
| 2009/0040754 A1 | 2/2009 | Brukilacchio et al. |
| 2009/0052185 A1 | 2/2009 | Toriyama et al. |
| 2009/0114799 A1 | 5/2009 | Maeda |
| 2009/0114803 A1 | 5/2009 | Yamaguchi |
| 2009/0122135 A1 | 5/2009 | Matsui |
| 2009/0122152 A1 | 5/2009 | Yamaguchi et al. |
| 2009/0124854 A1 | 5/2009 | Yamaguchi et al. |
| 2009/0153797 A1 | 6/2009 | Allon et al. |
| 2009/0181339 A1 | 7/2009 | Liang et al. |
| 2009/0201577 A1 | 8/2009 | LaPlante et al. |
| 2009/0218405 A1 | 9/2009 | Joseph et al. |
| 2009/0290149 A1 | 11/2009 | Roth |
| 2010/0065641 A1 | 3/2010 | Liu et al. |
| 2010/0087741 A1 | 4/2010 | Douplik et al. |
| 2010/0094136 A1 | 4/2010 | Nakaoka et al. |
| 2010/0110168 A1 | 5/2010 | Avni et al. |
| 2010/0110393 A1 | 5/2010 | Chen et al. |
| 2010/0121146 A1 | 5/2010 | Sugimoto |
| 2010/0125164 A1 | 5/2010 | LaBombard |
| 2010/0155487 A1 | 6/2010 | Liu et al. |
| 2010/0157039 A1 | 6/2010 | Sugai |
| 2010/0168588 A1 | 7/2010 | Matsumoto et al. |
| 2010/0198010 A1 | 8/2010 | Cline et al. |
| 2010/0208054 A1 | 8/2010 | Li |
| 2010/0277817 A1 | 11/2010 | Durell |
| 2010/0308116 A1 | 12/2010 | Sani et al. |
| 2011/0032350 A1 | 2/2011 | Kikuchi et al. |
| 2011/0073658 A1 | 3/2011 | Vassura et al. |
| 2011/0235017 A1 | 9/2011 | Iwasaki |
| 2011/0244506 A1 | 10/2011 | Sutter et al. |
| 2011/0270092 A1 | 11/2011 | Kang et al. |
| 2011/0290889 A1 | 12/2011 | Tamburini et al. |
| 2012/0006897 A1 | 1/2012 | Barkan et al. |
| 2012/0044462 A1 | 2/2012 | Kaji |
| 2012/0150046 A1 | 6/2012 | Watson et al. |
| 2012/0256002 A1 | 10/2012 | O'Donnell et al. |
| 2012/0319645 A1 | 12/2012 | O'Donnell et al. |
| 2013/0008964 A1 | 1/2013 | Hawley et al. |
| 2013/0237762 A1 | 9/2013 | Fengler et al. |
| 2014/0071328 A1 | 3/2014 | Miesak |
| 2014/0078378 A1 | 3/2014 | Demers et al. |
| 2014/0139893 A1 | 5/2014 | Sugiyama et al. |
| 2014/0187967 A1 | 7/2014 | Wood et al. |
| 2014/0194687 A1 | 7/2014 | Fengler et al. |
| 2015/0184811 A1 | 7/2015 | Moore |
| 2015/0230698 A1 | 8/2015 | Cline et al. |
| 2015/0320296 A1 | 11/2015 | Morita |
| 2015/0381909 A1 | 12/2015 | Butte et al. |
| 2016/0041098 A1 | 2/2016 | Hirawake et al. |
| 2016/0044253 A1 | 2/2016 | Dainty et al. |
| 2016/0100763 A1 | 4/2016 | Fengler et al. |
| 2016/0249019 A1 | 8/2016 | Westwick et al. |
| 2016/0360956 A1 | 12/2016 | Moore |
| 2017/0064257 A1 | 3/2017 | Westwick et al. |
| 2017/0064258 A1 | 3/2017 | Westwick et al. |
| 2017/0142314 A1 | 5/2017 | Moore et al. |
| 2017/0167980 A1 | 6/2017 | Dimitriadis et al. |
| 2017/0209050 A1 | 7/2017 | Fengler et al. |
| 2017/0354392 A1 | 12/2017 | Fengler et al. |

FOREIGN PATENT DOCUMENTS

| | | |
|---|---|---|
| CN | 201974160 U | 9/2011 |
| DE | 19535114 A1 | 3/1996 |
| DE | 19608027 A1 | 9/1996 |
| EP | 0512965 A1 | 11/1992 |
| EP | 0672379 A1 | 9/1995 |
| EP | 0774865 A2 | 5/1997 |
| EP | 0792618 A1 | 9/1997 |
| EP | 0671706 B1 | 6/1999 |
| EP | 1374755 A1 | 1/2004 |
| EP | 1883337 A1 | 2/2008 |
| EP | 2051603 A1 | 4/2009 |
| EP | 2859837 A1 | 4/2015 |
| FR | 2671405 A1 | 7/1992 |
| JP | S60-246733 A | 12/1985 |
| JP | S61-159936 A | 7/1986 |
| JP | H01-135349 A | 5/1989 |
| JP | 03-97439 A | 4/1991 |
| JP | 03-97441 A | 4/1991 |
| JP | 03-97442 A | 4/1991 |
| JP | 05-115435 A | 5/1993 |
| JP | 06-125911 A | 5/1994 |
| JP | H07-155285 A | 6/1995 |
| JP | H07-155286 A | 6/1995 |
| JP | H07-155290 A | 6/1995 |
| JP | H07-155291 A | 6/1995 |

(56) References Cited

FOREIGN PATENT DOCUMENTS

| | | |
|---|---|---|
| JP | H07-155292 A | 6/1995 |
| JP | H07-204156 A | 8/1995 |
| JP | H07-222712 A | 8/1995 |
| JP | H07-250804 A | 10/1995 |
| JP | H07-250812 A | 10/1995 |
| JP | H07-327913 A | 12/1995 |
| JP | H08-126605 A | 5/1996 |
| JP | 08-140928 A2 | 6/1996 |
| JP | 08-140929 A2 | 6/1996 |
| JP | H08-224208 A | 9/1996 |
| JP | H08-224209 A | 9/1996 |
| JP | H08-224210 A | 9/1996 |
| JP | H08-224240 A | 9/1996 |
| JP | H08-252218 A | 10/1996 |
| JP | H09-19408 A | 1/1997 |
| JP | 09-066023 A2 | 3/1997 |
| JP | 09-070384 A2 | 3/1997 |
| JP | H10-127563 A | 5/1998 |
| JP | H10-151104 A | 6/1998 |
| JP | 10-225427 A2 | 8/1998 |
| JP | H10-201700 A | 8/1998 |
| JP | H10-201707 A | 8/1998 |
| JP | H10-225426 A | 8/1998 |
| JP | H10-243915 A | 9/1998 |
| JP | H10-243920 A | 9/1998 |
| JP | H10-308114 A | 11/1998 |
| JP | H10-309281 A | 11/1998 |
| JP | H10-309282 A | 11/1998 |
| JP | H10-321005 | 12/1998 |
| JP | H10-328129 A | 12/1998 |
| JP | H11-47079 A | 2/1999 |
| JP | 11-089789 A2 | 4/1999 |
| JP | H11-104059 A | 4/1999 |
| JP | H11-104060 A | 4/1999 |
| JP | H11-104061 A | 4/1999 |
| JP | H11-104070 A | 4/1999 |
| JP | H11-155812 A | 6/1999 |
| JP | H11-113839 A | 7/1999 |
| JP | H11-244220 A | 9/1999 |
| JP | H11-332819 A | 12/1999 |
| JP | 2000-504968 A | 4/2000 |
| JP | 2000-245693 A | 9/2000 |
| JP | 2000-354583 A | 12/2000 |
| JP | 2001-78205 A | 3/2001 |
| JP | 2002-000560 A | 1/2002 |
| JP | 2002-049302 A | 2/2002 |
| JP | 2002-244122 A | 8/2002 |
| JP | 2003-045210 A | 2/2003 |
| JP | 2004-024611 A | 1/2004 |
| JP | 2004-094043 A | 3/2004 |
| JP | 2004-163902 A | 6/2004 |
| JP | 2004-520105 A | 7/2004 |
| JP | 2004-247156 A | 9/2004 |
| JP | 2004-289545 A | 10/2004 |
| JP | 2004-292722 A | 10/2004 |
| JP | 2005-010315 A | 1/2005 |
| JP | 2005-058618 A2 | 3/2005 |
| JP | 2005-058619 A2 | 3/2005 |
| JP | 2005-058620 A2 | 3/2005 |
| JP | 2005-080819 A2 | 3/2005 |
| JP | 2005-081079 A2 | 3/2005 |
| JP | 2005-149996 A | 6/2005 |
| JP | 2005-292404 A | 10/2005 |
| JP | 2006-073767 A | 3/2006 |
| JP | 2006-087764 A | 4/2006 |
| JP | 2006-525494 A | 11/2006 |
| JP | 2007-029453 A | 2/2007 |
| JP | 2007-072392 A | 3/2007 |
| JP | 2007-089840 A | 4/2007 |
| JP | 2010-107751 A | 5/2010 |
| JP | 2010-117442 A | 5/2010 |
| JP | 2010-524194 A | 7/2010 |
| JP | 2011-500921 A | 1/2011 |
| JP | 2011-072424 A | 4/2011 |
| JP | 2011-169819 A | 9/2011 |
| JP | 2011-528918 A | 12/2011 |
| JP | 5231625 B2 | 7/2013 |
| JP | 5859578 B2 | 2/2016 |
| RU | 99592 U1 | 11/2010 |
| WO | WO-1993/04648 A1 | 3/1993 |
| WO | WO-1994/13191 A1 | 6/1994 |
| WO | WO-1995/26673 A2 | 10/1995 |
| WO | WO-1998/24360 A1 | 6/1998 |
| WO | WO-1999/01749 A1 | 1/1999 |
| WO | WO-1999/53832 A1 | 10/1999 |
| WO | WO-2000/42910 A1 | 7/2000 |
| WO | WO-2000/54652 A1 | 9/2000 |
| WO | WO-2002/007587 A2 | 1/2002 |
| WO | WO-2002/50518 A2 | 6/2002 |
| WO | WO-2003/059159 A2 | 7/2003 |
| WO | WO-2003/059159 A8 | 7/2003 |
| WO | WO-2006/116847 A1 | 11/2006 |
| WO | WO-2007/081707 A2 | 7/2007 |
| WO | WO-2008/011722 A1 | 1/2008 |
| WO | WO-2008/0071240 A1 | 6/2008 |
| WO | WO-2009/033021 A2 | 3/2009 |
| WO | WO-2013/160279 A1 | 10/2013 |
| WO | WO-2014/176375 A2 | 10/2014 |
| WO | WO-2016/055837 A1 | 4/2016 |

OTHER PUBLICATIONS

R.F. Lyon & P.M Hubel, "Eyeing the Camera: Into the Next Century", 10 Color and Imaging Conference Final Program & Proceedings 349-355 (2002).*
Australian Examination Report No. 1 dated Jun. 28, 2018 for Australian Application No. 2016351730 filed on Nov. 10, 2016, five pages.
European Decision to Grant dated Jul. 12, 2018 for EP Application No. 12754208.2 filed Oct. 4, 2013, two pages.
European Decision to Grant dated May 25, 2018 for EP Patent Application No. 13180297.7 filed Aug. 13, 2013, two pages.
Indian Office Action dated Jun. 26, 2018 for Indian Patent Application No. 8678/DELNP/2013 filed on Mar. 8, 2012, five pages.
International Preliminary Report on Patentability dated May 24, 2018 for International Application No. PCT/CA2016/051315 filed on Nov. 10, 2016, nine pages.
U.S. Non Final Office Action dated Jun. 5, 2018, for U.S. Appl. No. 14/860,687, filed Sep. 21, 2015, eighteen pages.
U.S. Non Final Office Action dated Jun. 8, 2018, for U.S. Appl. No. 15/343,034, filed Nov. 3, 2016, thirteen pages.
U.S. Non Final Office Action dated May 25, 2018, for U.S. Appl. No. 15/343,038, filed Nov. 3, 2016, eleven pages.
Australian Office Action dated May 10, 2019 for Australian Patent Application No. 2016351730 filed Nov. 10, 2016, ten pages.
Canadian Office Action dated Feb. 19, 2019 for CA Patent Application No. 2,998,920 filed Mar. 16, 2018, four pages.
Chinese Office Action dated Sep. 26, 2018 for Chinese Patent Application No. 2018092001857100, filed on Sep. 4, 2017, nineteen pages.
European Notice of Allowance dated Mar. 18, 2019 for EP Patent Application No. 09819758.5, filed on May 4, 2011, seven pages.
International Preliminary Report on Patentability dated Dec. 27, 2018 for International Patent Application No. PCT/CA2017/050734 filed on Jun. 14, 2017, six pages.
U.S. Final Office Action dated Jan. 11, 2019 for U.S. Appl. No. 15/343,038, filed Nov. 3, 2016, twelve pages.
U.S. Final Office Action dated Jan. 14, 2019 for U.S. Appl. No. 14/860,687, filed Sep. 21, 2015, sixteen pages.
U.S. Final Office Action dated Jan. 22, 2019 for U.S. Appl. No. 15/343,034, filed Nov. 3, 2016, twelve pages.
U.S. Non Final Office Action dated Apr. 3, 2019 for U.S. Appl. No. 15/416,876, filed Jan. 26, 2017, thirteen pages.
U.S. Non Final Office Action dated Aug. 15, 2018 for U.S. Appl. No. 15/348,664, filed Nov. 10, 2016, eleven pages.
U.S. Non Final Office Action dated Feb. 5, 2019 for U.S. Appl. No. 15/623,100, filed Jun. 14, 2017, ten pages.

(56) References Cited

OTHER PUBLICATIONS

U.S. Appl. No. 15/810,911, filed Nov. 13, 2017. (Copy not submitted herewith pursuant to the waiver of 37 C.F.R. § 1.98(a)(2)(iii) issued by the Office on Sep. 21, 2004).
U.S. Restriction Requirement dated Feb. 7, 2019 for U.S. Appl. No. 29/562,795, filed Apr. 28, 2016, seven pages.
Australian Notice of Allowance dated Jun. 26, 2019 for Patent Application No. 2016351730 filed on Nov. 10, 2016, three pages.
Brazilian Office Action dated Aug. 5, 2019, for Patent Application No. BR1120130229977, filed Mar. 8, 2012, 4 pages (including English translation).
Canadian Office Action dated Nov. 5, 2019, for Canadian Patent Application No. 3027592, filed on Jun. 14, 2017, four pages.
European Extended Search Report dated Oct. 16, 2019, for Patent Application No. 17743524.5, filed Jan. 26, 2017, 4 pages.
European Extended Search Report dated May 7, 2019, for Patent Application No. 16863277.6, filed Nov. 10, 2016, 3 pages.
Japanese Office Action dated Jul. 12, 2019, for Patent Application No. 2018-51661, filed Nov. 10, 2016, 21 pages (including English translation).
Sensitization (photography), definition from Wikipedia, original language German, 6 pages (Machine Translation).
U.S. Final Office Action dated Jul. 25, 2019 for U.S. Appl. No. 15/416,876, filed Jan. 26, 2017, 13 pages.
U.S. Non-Final Office Action dated Sep. 27, 2019, for U.S. Appl. No. 29/562,795, filed Apr. 28, 2019, 6 pages.
European Notice of Allowance dated Feb. 28, 2018 for EP Patent Application No. 12754208.2 filed Oct. 4, 2013, six pages.
European Notice of Allowance dated Mar. 6, 2018 for EP Patent Application No. 13180297.7 filed Aug. 13, 2013, seven pages.
Indian Office Action dated Jan. 31, 2018 for Indian Patent Application No. 6532/DELNP/2010 filed on Sep. 16, 2010, five pages.
Japanese Notice of Allowance dated Apr. 2, 2018 for Japanese Patent Application No. 2017-018858 filed on Feb. 3, 2017, six pages.
Alfano, R.R. et al. (Oct. 1987). "Fluorescence Spectra From Cancerous and Normal Human Breast and Lung Tissues," *IEEE Journal of Quantum Electronics* QE-23(10):1806-1811.
Andersson-Engels, S. et al. (Mar. 1989). "Tissue Diagnostics Using Laser Induced Fluorescence," *Ber. Bunsenges Physical Chemistry* 93(3):335-342.
Bhunchet, E. et al. (Apr. 2002). "Fluorescein Electronic Endoscopy: A Novel Method for Detection of Early Stage Gastric Cancer Not Evident to Routine Endoscopy," *Gastrointestinal Endoscopy* 55(4):562-571.
Dawson, J.B. et al. (Jul. 1980). "A Theoretical and Experimental Study of Light Absorption and Scattering by In Vivo Skin," *Phys. Med. Biol.* 25(4):695-709.
Georgakoudi, I et al. (2003). "Quantitative Characterization of Biological Tissue Using Optical Spectroscopy," in Chapter 31 of *Biomedical Photonics Handbook*, Tuan Vo-Dinh (ed.), CRC Press, New York, thirty three pages.
Georgakoudi, I et al. (Apr. 2005). "Characterization of Dysplastic Tissue Morphology and Biochemistry in Barrett's Esophagus using Diffuse Reflectance and Light Scattering Spectroscopy," *Techniques in Gastrointestinal Endoscopy* 7(2):100-105.
Hubel, P.M. et al. (2004). "Spatial Frequency Response of Color Image Sensors: Bayer Color Filters and Foveon X3," *Proceedings of SPIE* 5301:402-406.
Hung, J. et al. (1991). "Autofluorescence of Normal and Malignant Bronchial Tissue," *Lasers in Surgery and Medicine* 11(2):99-105.
Török, B. et al. (May 1996). "Simultane digitale Indocyaningrün— und Fluoreszeinangiographie (Simultaneous Digital ICG and Fluorescein Angiography)," *Klin Monatsbl Augenheilkd* 208(5):333-336, (with English Translation of the Introduction).
Canadian Examiner's Report for Registration of an Industrial Design dated Feb. 1, 2017 for Canadian Application No. 171282, filed on Oct. 27, 2016, two pages.
Chinese Notice of Allowance dated Jun. 19, 2017 for Chinese Application No. 201280022284.3, filed on Nov. 7, 2013, four pages.

Chinese Office action dated Jul. 29, 2016 for application No. 2012800222843 filed on Mar. 8, 2012, eight pages.
Chinese Office action dated Nov. 24, 2015 for application No. 2012800222843 filed on Mar. 8, 2012, sixteen pages.
Chinese Third Office Action dated Mar. 14, 2017 for Chinese Patent Application No. 201280022284.3, filed on Nov. 7, 2013, seven pages.
European Communication Pursuant to Article 94(3) EPC dated Apr. 13, 2017, filed on Oct. 4, 2013, five pages.
European Communication pursuant to Rules 70(2) and 70a(2) EPC and Reference to Rule 39(1) EPC dated Jan. 23, 2017 for European Application No. 16186321.2 filed on Aug. 30, 2016, two pages.
European Communication under Rule 71(3) EPC dated Nov. 25, 2016 for EP Application No. 08706262.6 filed on Aug. 21, 2009, eight pages.
European Decision to Grant a European Patent Pursuant to Article 97(1) EPC dated Jun. 22, 2017, for EP Application No. 08706262.6 filed on Aug. 21, 2009, two pages.
European Extended Search Report dated Jul. 17, 2014, for EP Application No. 09721252.6 filed Mar. 18, 2009; eleven pages.
European Extended Search Report dated Sep. 20, 2013, for EP Application No. 08706262.6 filed on Jan. 23, 2008, five pages.
European Invitation Pursuant to Article 94(3) and Rule 71(1) EPC dated Apr. 6, 2017, for EP Application No. 09819758.5, filed on May 4, 2011, five pages.
European Office Action dated Dec. 3, 2015, for EP Application No. 08706262.6 filed on Jan. 23, 2008; fifteen pages.
European Office Action dated Nov. 19, 2015, for EP Application No. 07 785 001.4, filed on Jul. 30, 2007, four pages.
European Office Action dated Nov. 3, 2015 for EP Patent Application No. 12754208.2 filed Oct. 4, 2013, four pages.
European Office Action dated Sep. 29, 2015, for EP Application No. 09721252.6 filed Mar. 18, 2009; five pages.
European Search Report and Written Opinion dated Dec. 21, 2016 for European Application No. 16186321.2 filed on Aug. 30, 2016, nine pages.
European Supplemental Search Report dated Jan. 24, 2012, for European Patent Application No. 07785001.4 filed on Jul. 30, 2007, seven pages.
European Supplemental Search Report dated Oct. 1, 2014 for EP Application No. 12754208.2 filed on Mar. 8, 2012, five pages.
European Supplemental Search Report dated Oct. 9, 2013, for European Patent Application No. 06721854.5, filed on May 4, 2005, six pages.
Extended European Search Report dated Jan. 24, 2012 for EP Application No. 07 785 001.4, filed on Jul. 30, 2007, seven pages.
International Preliminary Report on Patentability dated Feb. 3, 2009, for International Application No. PCT/CA2007/001335 filed on Jul. 30, 2007, five pages.
International Preliminary Report on Patentability dated Nov. 6, 2007, for International Application No. PCT/CA2006/000669, filed on Apr. 27, 2006, nine pages.
International Preliminary Report on Patentability dated Sep. 21, 2010, for International Application No. PCT/US2009/037506, filed on Mar. 18, 2009, seven pages.
International Search Report and written Opinion dated Apr. 24, 2017, for International Application No. PCT/CA2017/050083, filed on Jan. 26, 2017, seven pages.
International Search Report and Written Opinion dated Sep. 18, 2017, for International Application No. PCT/CA2017/050734, filed on Jun. 14, 2017, eight pages.
International Search Report and Written Opinion of the International Searching Authority dated Feb. 10, 2017, for International Application No. PCT/CA2016/051315 filed on Nov. 10, 2016, thirteen pages.
International Search Report dated Aug. 3, 2006, for International Application No. PCT/CA2006/000669, filed on Apr. 27, 2006, three pages.
International Search Report dated Aug. 3, 2012, for International Application No. PCT/162012/000601, filed on Mar. 8, 2012, three pages.

(56) References Cited

OTHER PUBLICATIONS

International Search Report dated Dec. 7, 2007, for International Application No. PCT/CA2007/001335, filed on Jul. 30, 2007, two pages.
International Search Report dated Jan. 21, 2002, for International Application No. PCT/US2001/022198, filed on Jul. 13, 2001, three pages.
International Search Report dated Jul. 22, 2009, for International Application No. PCT/US09/37506, filed on Mar. 18, 2009, two pages.
International Search Report dated May 13, 2008 for Intentional Application No. PCT/CA2008/00015, filed on Jan. 8, 2008, one page.
Invitation to Pay additional Fees and, where Applicable, Protest Fee, dated Dec. 22, 2016 for International Application No. PCT/CA2016/051315, filed on Nov. 10, 2016, two pages.
Japanese Final Office Action dated Aug. 2, 2013, for Japanese Patent Application No. 2008-509275, filed on Apr. 27, 2006, four pages.
Japanese Office Action dated Dec. 8, 2017 for Japanese Patent Application No. 2017-018858 filed on Feb. 3, 2017, six pages.
Japanese Notice of Allowance dated Jan. 5, 2017 in Japanese Patent Application No. 2015-238784, filed on Dec. 7, 2015, six pages.
Japanese Notice of Allowance dated Nov. 17, 2017, for Japanese Patent Application No. 2016-253736 filed on Dec. 27, 2016, six pages.
Japanese Notice of Allowance dated Nov. 28, 2016 for Japanese Patent Application No. 2015-245598, filed on Mar. 8, 2012, six pages.
Japanese Office Action dated Apr. 20, 2012, issued in counterpart Japanese Application No. 2011-500921, filed Mar. 18, 2009, four pages.
Japanese Office Action dated Apr. 3, 2015 in Japanese Application No. 2013-058356 filed Mar. 18, 2009, four pages.
Japanese Office Action dated Feb. 17, 2012, for Japanese Patent Application No. 2008-509275, filed on Apr. 27, 2006, six pages.
Japanese Office Action dated Jul. 22, 2014 for Japanese Patent Application No. 2013- 557187 filed Mar. 8, 2012, seven pages.
Japanese Office Action dated Mar. 9, 2015 for Japanese Patent Application No. 2013- 557187, filed Mar. 8, 2012, five pages.
Japanese Office Action dated Nov. 11, 2011, for Japanese Patent Application No. 2009-521077, filed on Jul. 30, 2007, four pages.
Japanese Office Action dated Sep. 14, 2012, for Japanese Patent Application No. 2008-509275, filed on Apr. 27, 2006, seven pages.
Japanese Office Action dated Sep. 19, 2014, for Japanese Patent Application No. 2013-246636, filed on Apr. 27, 2006, six pages.
Japanese Office dated Dec. 26, 2012 for Japanese Patent Application No. 2011-500921, filed on Mar. 18, 2009, two pages.
Japanese Patent Office Action dated May 26, 2014 in Japanese Patent Application No. 2013-058356, filed on Mar. 18, 2009, three pages.
Korean Decision of Refusal Action dated Aug. 30, 2016 for patent application No. 10-2015-7033310 filed on Mar. 8, 2012, seven pages.
Korean Decision on the Trial Against Final Rejection from the Intellectual Property Tribunal (IPT) dated Sep. 25, 2017, for Korean Patent Application No. 2013-7026479, filed on Oct. 7, 2013, seventeen pages.
Korean Notice of Allowance dated Jan. 2, 2017 for Korean Application No. 10-2015-7033310, filed on Nov. 20, 2015, three pages.
Korean Office Action dated Aug. 20, 2015 for patent application No. 20137026479 filed on Mar. 8, 2012, three pages.
Korean Office Action dated Dec. 8, 2015 for patent application No. 20157033310 filed on Mar. 8, 2012, seven pages.
Korean Office Action dated Jun. 27, 2017 for Korean Patent Application No. 2017-7008654, filed on Mar. 29, 2017, ten pages.
Korean Notice of Allowance dated Dec. 13, 2017 for Korean Patent Application No. 10-2017-7008654, filed on Mar. 29, 2017, three pages.
Russian Office Action—Decision to Grant dated Aug. 19, 2016 for Russian Patent Application No. 2013144845/07, filed on Mar. 8, 2012, thirteen pages.
U.S. Final Office Action dated Apr. 24, 2015 for U.S. Appl. No. 12/933,512, filed Nov. 24, 2010, nineteen pages.
U.S. Final Office Action dated Aug. 10, 2017, for U.S. Appl. No. 15/343,034, filed Nov. 3, 2016, twelve pages.
U.S. Final Office Action dated Aug. 11, 2017, for U.S. Appl. No. 14/860,687, filed Sep. 21, 2015, seventeen pages.
U.S. Final Office Action dated Aug. 7, 2017, for U.S. Appl. No. 15/343,038, filed Nov. 3, 2016, eleven pages.
U.S. Final Office Action dated Feb. 27, 2017 for U.S. Appl. No. 15/247,419 filed Aug. 25, 2016, ten pages.
U.S. Final Office Action dated Jul. 23, 2008, for U.S. Appl. No. 11/122,267 filed May 4, 2016, six pages.
U.S. Final Office Action dated Jun. 18, 2015, for U.S. Appl. No. 14/154,177, filed Jan. 13, 2014, eight pages.
U.S. Final Office Action dated Jun. 5, 2014, for U.S. Appl. No. 12/761,462, filed Apr. 16, 2010, fourteen pages.
U.S. Final Office Action dated Mar. 22, 2016 for U.S. Appl. No. 14/873,842, filed Oct. 2, 2015, eighteen pages.
U.S. Final Office Action dated May 11, 2011, for U.S. Appl. No. 11/412,715, filed Apr. 26, 2006, eight pages.
U.S. Final Office Action dated May 21, 2012, for U.S. Appl.No. 11/964,330, filed Dec. 26, 2007, twelve pages.
U.S. Final Office Action dated Nov. 24, 2009, for U.S. Appl. No. 11/009,965, filed Dec. 10, 2004, fourteen pages.
U.S. Non Final Office Action dated Apr. 2, 2009, for U.S. Appl. No. 11/009,965, filed Dec. 10, 2004, thirteen pages.
U.S. Non Final Office Action dated Aug. 16, 2013, for U.S. Appl. No. 12/761,462, filed Apr. 16, 2010, ten pages.
U.S. Non Final Office Action dated Aug. 16, 2013, for U.S. Appl. No. 12/761,523, filed Apr. 16, 2010, nine pages.
U.S. Non Final Office Action dated Dec. 10, 2010, for U.S. Appl. No. 11/412,715, filed Apr. 26, 2006, ten pages.
U.S. Non Final Office Action dated Dec. 14, 2011, for U.S. Appl. No. 11/412,715, filed Apr. 26, 2006, eight pages.
U.S. Non Final Office Action dated Feb. 1, 2017, for U.S. Appl. No. 14/860,687, filed Sep. 21, 2015, sixteen pages.
U.S. Non Final Office Action dated Feb. 3, 2010, for U.S. Appl. No. 11/626,308, filed Jan. 23, 2007, eleven pages.
U.S. Non Final Office Action dated Jan. 2, 2008, for U.S. Appl. No. 11/122,267, filed May 4, 2005, five pages.
U.S. Non Final Office Action dated Jan. 20, 2016, for U.S. Appl. No. 14/629,473, filed Feb. 23, 2015, fifteen pages.
U.S. Non Final Office Action dated Jan. 26, 2017, for U.S. Appl. No. 15/343,034, filed Nov. 3, 2016, seventeen pages.
U.S. Non Final Office Action dated Jan. 27, 2017, for U.S. Appl. No. 15/343,038, filed Nov. 3, 2016, fifteen pages.
U.S. Non Final Office Action dated Jul. 17, 2003, for U.S. Appl. No. 09/905,642, filed Jul. 13, 2001, six pages.
U.S. Non Final Office Action dated Jul. 2, 2013 for U.S. Appl. No. 12/933,512, filed Nov. 24, 2010, twelve pages.
U.S. Non Final Office Action dated Jun. 1, 2007, for U.S. Appl. No. 10/899,648, filed Jul. 26, 2004, seven pages.
U.S. Non Final Office Action dated Jun. 20, 2008, for U.S. Appl. No. 11/009,398, filed Dec. 10, 2004, fifteen pages.
U.S. Non Final Office Action dated Jun. 23, 2010, for U.S. Appl. No. 11/009,965, filed Dec. 10, 2004, fifteen pages.
U.S. Non Final Office Action dated Jun. 27, 2014 for U.S. Appl. No. 13/415,561, filed Mar. 3, 2012, fourteen pages.
U.S. Non Final Office Action dated Jun. 9, 2011, for U.S. Appl. No. 11/830,323, filed Jul. 30, 2007, five pages.
U.S. Non Final Office Action dated May 18, 2004, for U.S. Appl. No. 10/050,601, filed Jan. 15, 2002, eight pages.
U.S. Non Final Office Action dated Nov. 23, 2009, for U.S. Appl. No. 11/969,974, filed Jan. 7, 2008, seven pages.
U.S. Non Final Office Action dated Nov. 5, 2014, for U.S. Appl. No. 13/930,225, filed Jun. 28, 2013, six pages.
U.S. Non Final Office Action dated Oct. 23, 2013 for U.S. Appl. No. 13/415,561, filed Mar. 8, 2012, ten pages.
U.S. Non Final Office Action dated Oct. 5, 2016 for U.S. Appl. No. 15/247,419, filed Aug. 25, 2016, eight pages.

(56) References Cited

OTHER PUBLICATIONS

U.S. Non Final Office Action dated Oct. 7, 2011, for U.S. Appl. No. 11/964,330, filed Dec. 26, 2007; ten pages.
U.S. Non Final Office Action dated Sep. 12, 2014, for U.S. Appl. No. 14/154,177, filed On Jan. 13, 2014, four pages.
U.S. Non Final Office Action dated Sep. 6, 2016 for U.S. Appl. No. 14/873,842, filed Oct. 2, 2015, seven pages.
U.S. Non Final Office Action with Restriction Requirement dated Mar. 4, 2011, for U.S. Appl. No. 11/830,323, filed Jul. 30, 2007, nine pages.
U.S. Notice of Allowance dated Dec. 30, 2016, for U.S. Appl. No. 14/873,842, filed Oct. 2, 2015, eleven pages.
U.S. Notice of Allowance dated Apr. 7, 2004, for U.S. Appl. No. 09/905,642, filed Jul. 13, 2001, six pages.
U.S. Notice of Allowance dated Aug. 26, 2004, for U.S. Appl. No. 10/050,601, filed Jan. 15, 2002, eight pages.
U.S. Notice of Allowance dated Aug. 6, 2015, for U.S. Appl. No. 13/853,656, filed Mar. 29, 2013, seven pages.
U.S. Notice of Allowance dated Dec. 10, 2012, for U.S. Appl. No. 11/964,330, filed Dec. 26, 2007, seven pages.
U.S. Notice of Allowance dated Feb. 25, 2010, for U.S. Appl. No. 11/969,974, filed Jan. 7, 2008, four pages.
U.S. Notice of Allowance dated Jan. 2, 2008, for U.S. Appl. No. 10/899,648, filed Jul. 26, 2004, three pages.
U.S. Notice of Allowance dated Jul. 10, 2017 for U.S. Appl. No. 15/247,419 filed Aug. 25, 2016, eight pages.
U.S. Notice of Allowance dated Jun. 25, 2015, for U.S. Appl. No. 12/933,512, filed Nov. 24, 2010 fourteen pages.
U.S. Notice of Allowance dated Mar. 22, 2013, for U.S. Appl. No. 11/964,330, filed Dec. 26, 2007, eight pages.
U.S. Notice of Allowance dated Mar. 28, 2016, for U.S. Appl. No. 13/853,656, filed Mar. 29, 2013, eight pages.
U.S. Notice of Allowance dated May 18, 2015, for U.S. Appl. No. 13/930,225, filed Jun. 28, 2013, nine pages.
U.S. Notice of Allowance dated Nov. 23, 2015, for U.S. Appl. No. 13/853,656, filed Mar. 29, 2013, seven pages.
U.S. Notice of Allowance dated Oct. 10, 2014, for U.S. Appl. No. 12/761,462, filed Apr. 16, 2010, ten pages.
U.S. Notice of Allowance dated Oct. 5, 2007, for U.S. Appl. No. 10/899,648, filed Jul. 26, 2004, six pages.
U.S. Notice of Allowance dated Sep. 10, 2013, for U.S. Appl. No. 11/412,715, filed Apr. 26, 2006, eight pages.
U.S. Notice of Allowance dated Sep. 14, 2012, for U.S. Appl. No. 11/830,323, filed Jul. 30, 2007, eight pages.
U.S. Supplemental Notice of Allowability dated Mar. 10, 2005, for U.S. Appl. No. 10/050,601, filed Jan. 15, 2002, five pages.
Written Opinion of the International Searching Authority dated Aug. 3, 2006, for International Application No. PCT/CA2006/000669, filed on Apr. 27, 2006, eight pages.
Written Opinion of the International Searching Authority dated Dec. 7, 2007, for International Application No. PCT/CA2007/001335, filed on Jul. 30, 2007, four pages.

\* cited by examiner

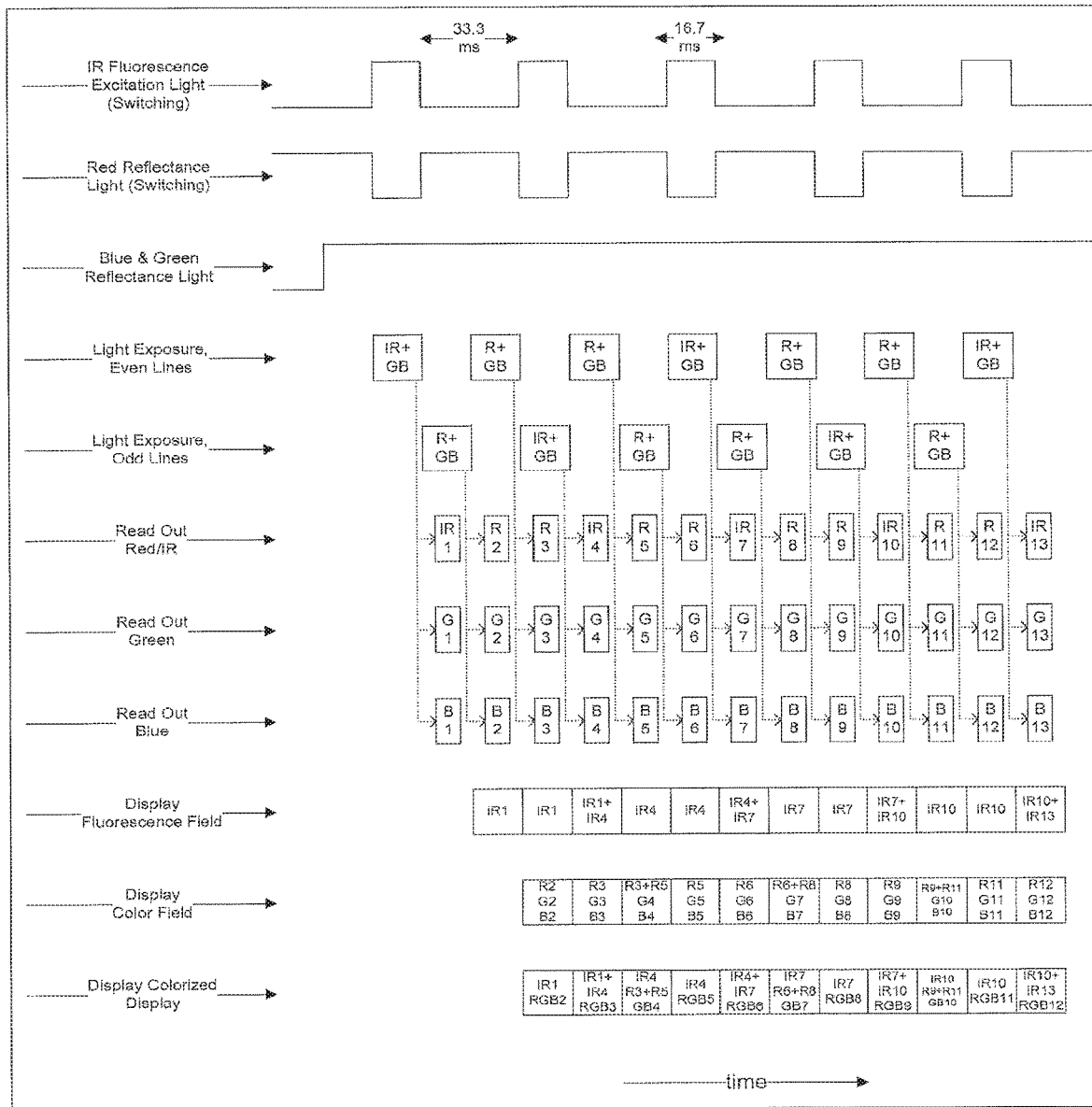
Fig 4 Interlaced Read-out Scheme

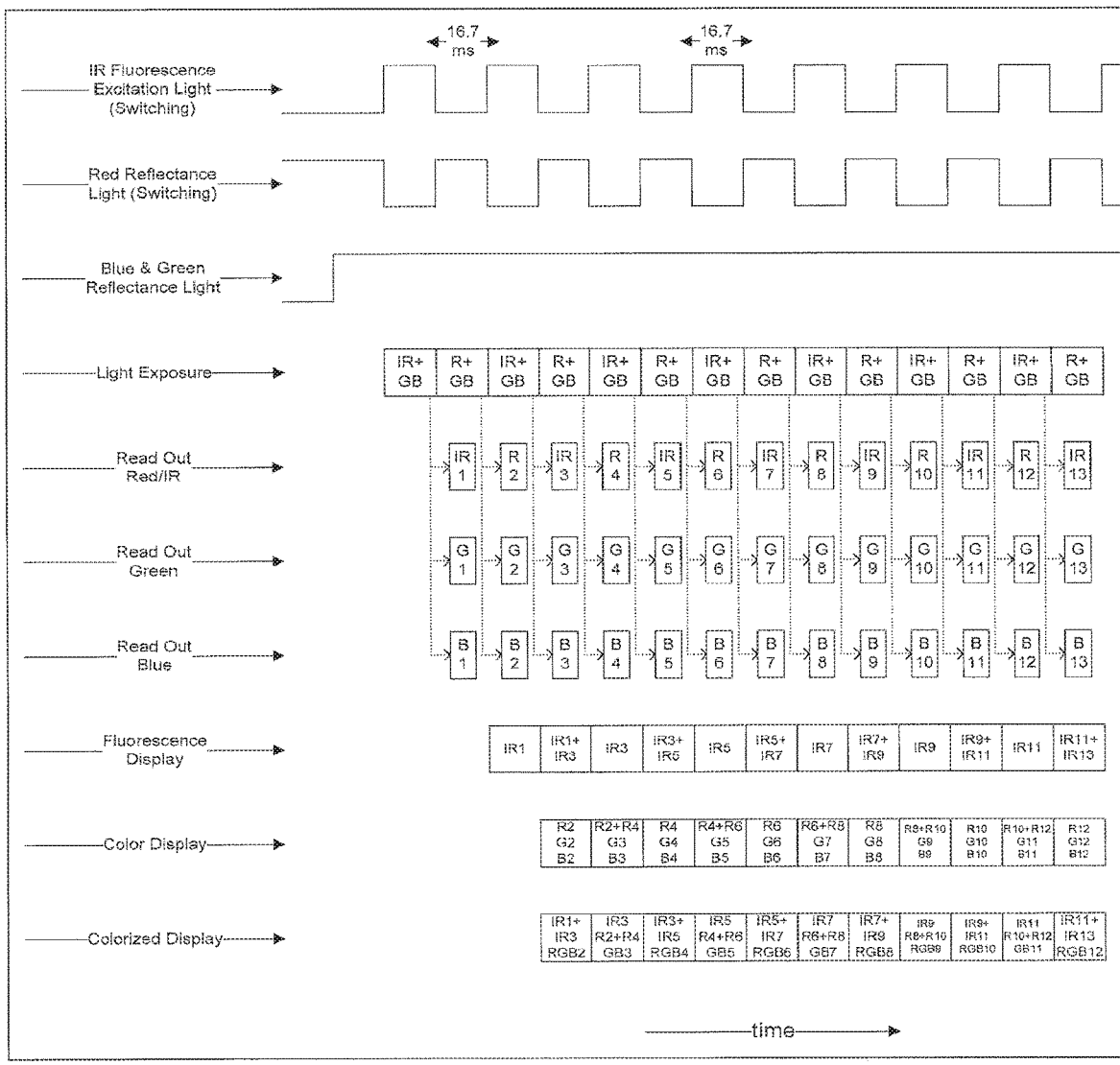
Fig 5 Progressive Scan Scheme

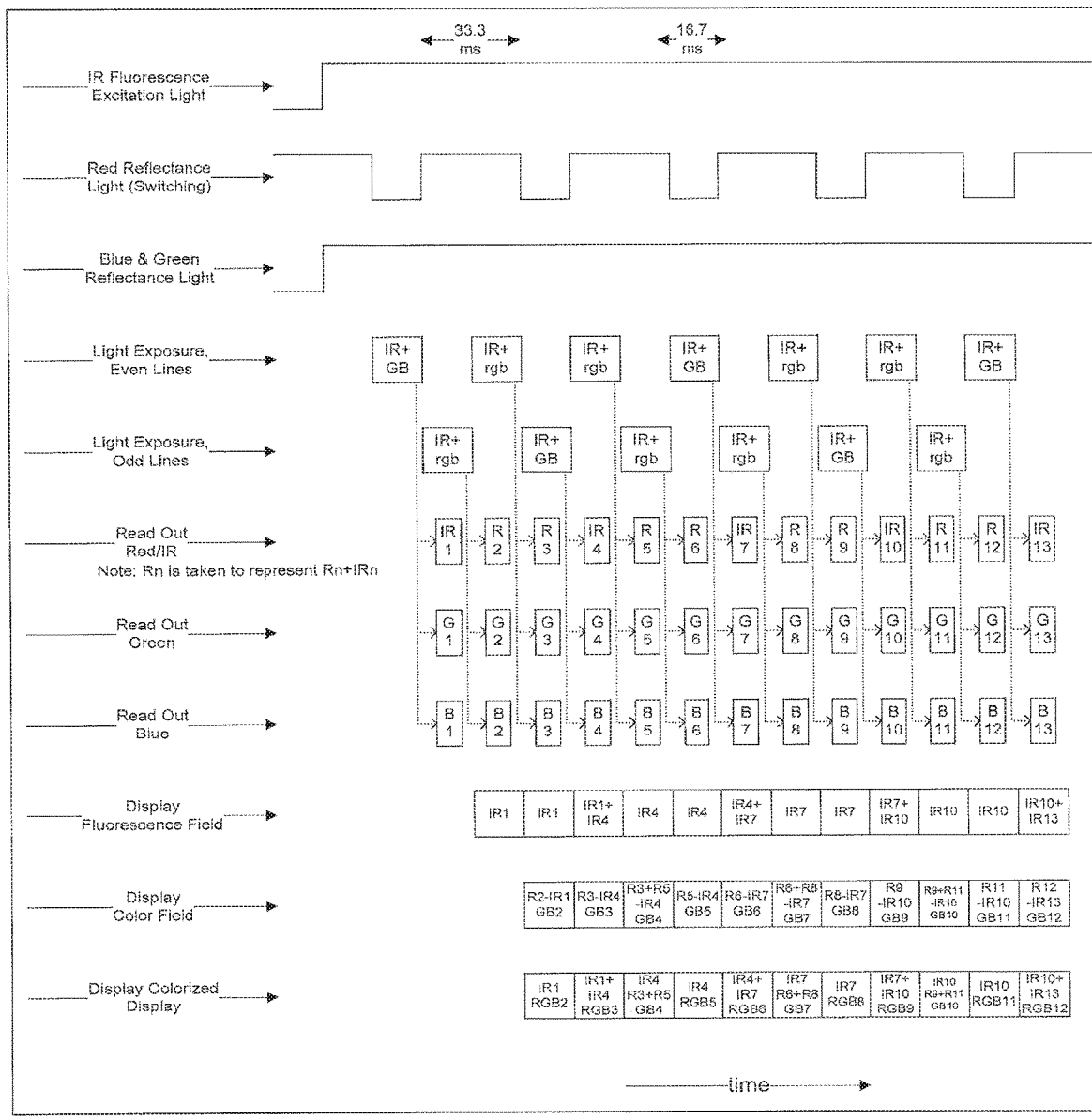
Fig 6 Interlaced, with continuous NIR Scheme

IMAGING SYSTEM FOR COMBINE FULL-COLOR REFLECTANCE AND NEAR-INFRARED IMAGING

CROSS-REFERENCE TO RELATED APPLICATIONS

This application is a continuation of U.S. application Ser. No. 14/873,842, filed Oct. 2, 2015, which is a continuation of U.S. application Ser. No. 12/933,512, filed Nov. 24, 2010, now U.S. Pat. No. 9,173,554, which is the U.S. national phase application of PCT/US2009/037506, having an international filing date of Mar. 18, 2009, which claims the benefit of U.S. Provisional Application No. 61/037,514, filed Mar. 18, 2008, each of which are incorporated herein by reference in their entirety.

FIELD OF THE INVENTION

The invention is directed to medical imaging, in particular to a system and method for obtaining visible light images and near infrared light images from an area under observation, such as living tissue, and in particular for use in endoscopy.

BACKGROUND OF THE INVENTION

Near-infrared (NIR) imaging has been described in the literature for various clinical applications. Typically such an imaging modality utilizes a contrast agent (e.g. indocyanine green) that absorbs and/or fluoresces in the NIR. Such contrast agents may be conjugated to targeting molecules (e.g. antibodies) for disease detection. The contrast agents may be introduced into tissue intravenously or subcutaneously to image tissue structure and function (e.g. flow of blood/lymph/bile in vessels) that is not easily seen with standard visible light imaging technology.

Independently of the clinical application, endoscopic NIR imaging devices typically include multiple imaging modes as a practical feature. For example, endoscopists utilize visible spectrum color for both visualization and navigation, and an endoscopic imaging device that offers NIR imaging typically provides a concurrent color image. Such concurrent imaging devices can be realized, for example, as follows:

One conventional configuration utilizes spectral separation of the visible and the NIR light, with full color and NIR image signals acquired using separate sensors for the different color (e.g. red, green, and blue) and NIR spectral bands or a single color sensor with an integrated filter with filter elements transparent to the different spectral bands (e.g. red, green, blue and NIR). Thus, such multi-modality color and NIR imaging devices provide dedicated sensors or sensor pixels for each of the two imaging modes. Disadvantageously, this increases the number of image sensors in multi-sensor implementations or compromises image resolution when on the same sensor, specific sensor pixels are dedicated for NIR imaging while others are utilized for color imaging.

Another conventional configuration utilizes a single monochrome image sensor for sequential imaging of the visible and NIR light. The object is hereby sequentially illuminated with light in the red, green, blue and NIR spectral bands, with separate image frames being acquired for each spectral band and composite color and NIR images being generated from the acquired image frames. However, this approach, where image frames are acquired sequentially at different times, can generate objectionable motion artifacts (i.e. color fringing and "rainbow effects") in the composite color and NIR images. These artifacts can be mitigated by increasing the acquisition or frame rate to more than, for example, 15 frames/second (fps), for example to 90 fps, or even 180 fps. Because of the high data transfer rate, high frame rates are difficult to implement for high definition images (e.g. 2 million pixels), or images having a large dynamic range (>10 bits), thus limiting image size and/or resolution.

It would therefore be desirable to provide a system and a method for simultaneous acquisition of full-color visible light and NIR light images, which obviates the aforementioned disadvantages and does not compromise image resolution and/or introduce objectionable motion artifacts.

SUMMARY OF THE INVENTION

According to one aspect of the invention, a method for acquisition of NIR images and full-color images includes the steps of illuminating an area under observation with continuous blue/green light, and illuminating the area under observation with red light and NIR light, wherein at least one of the red light and NIR light are switched on and off periodically. The blue, green, red and NIR light returning from the area under observation is directed to one or more sensors which are configured to separately detect the blue light, the green light, and the combined red light /NIR light. The red light spectral component and the NIR light spectral component are determined separately from image signals of the combined red light /NIR light, in synchronism with the switched red and NIR light. A full-color reflectance image of the area under observation is rendered and displayed from the blue, green, and red light and an NIR image is likewise rendered and displayed from the NIR light.

According to another aspect of the invention, an imaging system for acquisition of NIR and full-color images includes a light source providing visible light and NIR light to an area under observation, a camera having one or more image sensors configured to separately detect blue and green light, and combined red and NIR light returned from the area under observation, and a controller in signal communication with the light source and the camera. The controller is configured to control the light source to continuously illuminate tissue with blue/green light and to illuminate the area under observation with red light and NIR light, wherein at least one of the red light and NIR light are switched on and off periodically in synchronism with the acquisition of the red and NIR images in the camera.

The controller is further configured to determine from sensor signals representing the combined red light and NIR light separately the red light spectral component and the NIR light spectral component. The imaging system further includes a display receiving image signals corresponding to the blue light, the green light, and the separately determined red light spectral component and rendering therefrom a full-color visible light image of the area under observation. The display also receives the separately determined NIR light spectral component and renders therefrom an NIR image of the area under observation.

The video imaging system may use a three-sensor color camera configured to continuously image the blue and green wavebands and intermittently image the red waveband, thus providing continuous, high quality luma information and a sufficiently continuous complete chroma to produce high quality video images of the area under observation, such as living tissue. In such a configuration, the red image sensor can be time-multiplexed to acquire both red and NIR images (i.e. the red image sensor alternately, and in rapid succession, images both red light for the color information required for the color image and NIR light for image information required for the NIR image). Such time-multiplexing may be coupled to (and synchronized with) the illumination source used to provide the NIR illumination (excitation for fluorescence) and the red light for color imaging. Image processing is then utilized to separate and process the resulting image signals appropriately.

Embodiments of the invention may include one or more of the following features. The area under observation may be alternatingly illuminated with red light and NIR light, wherein the duration of red light may be different from, preferably longer than, the duration of illumination with NIR light. The illumination may be switched at video field or frame rates.

Fields captured by the image sensor and lacking the red light spectral component or the NIR light spectral component may be interpolated from temporally adjacent image fields that include a corresponding red light spectral component or NIR light spectral component. In one embodiment, the NIR light spectral component obtained in the absence of red light may be subtracted from the combined red light /NIR light to obtain the separate red light spectral component. This is advantageous in particular when the detected NIR signal has an intensity comparable to that of the red signal.

In one embodiment, the light source may include an illuminator emitting a substantially constant intensity of visible light and NIR light over a continuous spectral range, and a plurality of movable filters disposed between the illuminator and the area under observation for transmitting temporally continuous blue/green light and temporally discontinuous red light and NIR light.

In another embodiment, the light source may include an illuminator emitting a substantially constant intensity of visible light and NIR light over a continuous spectral range, first dichroic means for separating the visible light and NIR light into blue/green and red light and NIR light, shutter means for transforming the separated red light and NIR light into temporally discontinuous red light and discontinuous NIR light, and second dichroic means for combining the blue/green light, the temporally discontinuous red light and the temporally discontinuous NIR light for transmission to the area under observation.

In yet another embodiment, the light source may include a first illuminator emitting a substantially constant intensity of green and blue light, a second illuminator producing switched red light, a third illuminator producing switched NIR excitation light, and dichroic means for combining the switched red light and the switched NIR light with the green and blue light for transmission to the area under observation. The switched red light and the NIR light may be produced by interrupting a continuous intensity light beam of the red light and the NIR light by a shutter or chopper. Alternatively, the switched red light and the NIR light may be produced by electrically switching the second illuminator and the third illuminator on and off.

The image sensors may employ an interlaced scan or a progressive scan.

The imaging system may include an endoscope.

BRIEF DESCRIPTION OF THE DRAWINGS

The following figures depict certain illustrative embodiments of the invention which are to be understood as illustrative of the invention and not as limiting in any way.

FIG. 3b shows the optical transmission ranges for the spectral components separated by the dichroic prism of FIG. 3a;

FIG. 4 shows a timing diagram of a first embodiment for continuous illumination with green/blue light and alternating illumination with red/NIR light;

FIG. 5 shows a timing diagram of a second embodiment for continuous illumination with green/blue light and alternating illumination with red/NIR light;

FIG. 6 shows a timing diagram of a third embodiment for continuous illumination with green/blue/NIR light and alternating illumination with red light;

DESCRIPTION OF CERTAIN ILLUSTRATED EMBODIMENTS

Color video images are generally obtained with three-sensor color cameras where separate red, green and blue image sensors provide simultaneous contiguous arrays of red, green and blue pixel information. Full color video images are generated by combining the image information from all three sensors. Color fidelity (i.e. a true color rendition) is extremely important in medical imaging applications and all three sensors are used to provide complete color information.

To understand the relative importance of color and spatial information in video images of human tissue, however, it is useful to consider information in such video images in terms of luma and chroma. Luma refers to the brightness information in the image and it is this information that provides the spatial detail that enables the viewer to recognize shapes. The spatial and temporal resolution of luma is consequently crucial to the perception of video image quality. Chroma refers to the color information in the video image. It is a property of human vision that fine detail variations in the chroma of image features are not easily perceived and that such variations are consequently less critical than fine detail variations in luma, in an overall assessment of image quality. It is for this reason that video encoding of chroma information is often sub-sampled.

In video images of human tissue obtained with visible light, the structural details of the tissue are largely contained in the blue and green wavelength regions of the imaged light. Blue and green light tends to be reflected from the tissue surface, whereas red light tends to be highly scattered within the tissue. As a consequence, there is very little fine structural detail in the red light that reaches the red image sensor. It is also known from color science that human vision receives most of the spatial information from the green portion of the visible spectrum—i.e. green light information contributes disproportionately to the luma. The standard formula for calculating luma from gamma-corrected color components is $Y'=0.2126 R'+0.7152 G'+0.0722 8'$. For this reason, spatial and/or temporal interpolation of the red component of video images of human tissue does not significantly affect perception of fine detail in those images.

Similarly to red light, NIR light tends to be scattered in tissue causing NIR image features to be diffusely, rather than sharply defined. Furthermore, because the NIR image highlights areas of interest (i.e. the areas in which the contrast agent is localized), but does not provide the overall visualization or navigational information, it is desirable for a NIR endoscopic imaging device to provide a continuous color image and either a superimposed or side-by-side display of the NIR image information. In such a display the NIR light would also contribute less to the spatial information presented to observer.

Figure 1:
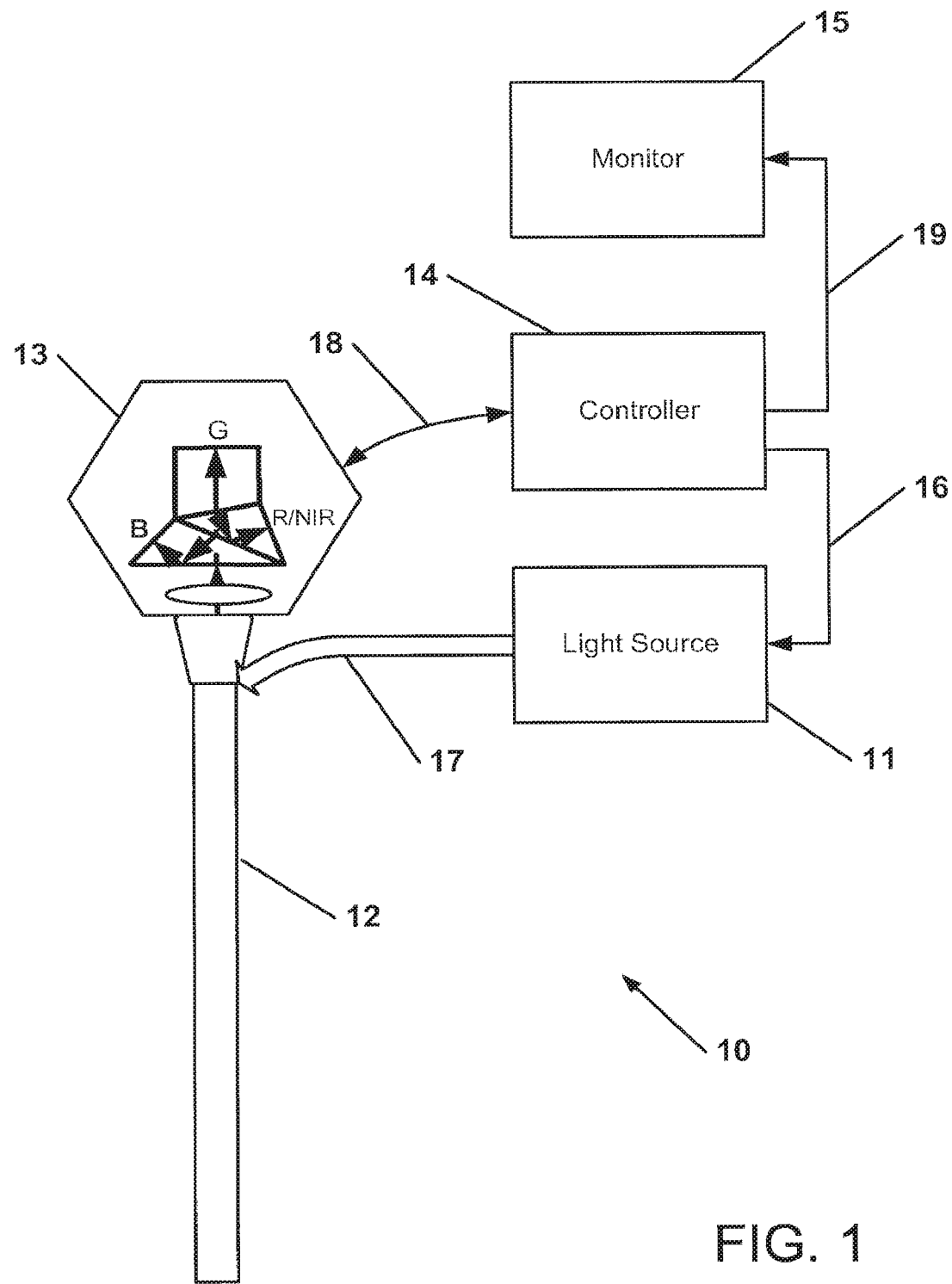
FIG. 1 shows an endoscopic system according to one embodiment of the invention.

FIG. 1 shows schematically an exemplary embodiment of a NIR endoscopic imaging system 10 which includes a multimode light source 11 that provides both visible and NIR illumination, connected to an endoscope 12 by way of an illumination guide, for example a fiber optic cable 17, suitable for transmission of both color and NIR illumination, a color camera 13, illustrated here as having three different sensors 34, 36, 38 (see FIG. 3a) for blue, green and red/NIR imaging, respectively, mounted to the endoscope image guide, and a camera controller 14 connected to the camera 13 and the light source 11 for controlling and synchronizing illumination and image acquisition. Controller 14 can also process the acquired visible and NIR images for display on a monitor 15 connected to the controller 14, for example, by a cable 19. Images can be acquired in real time at selectable frame rates, such as video rates.

FIGS. 2a-2d show schematic diagrams of exemplary embodiments of various light sources 11. The illustrated light sources are constructed to supply in normal color imaging mode visible illumination light yielding a substantially continuous spectral distribution. The light source maybe an arc lamp, a halogen lamp, one or more solid state sources (e.g. LEDs, semiconductor lasers) or any combination thereof and may be spectrally filtered or shaped (e.g. with bandpass filters, IR filters, etc.). The continuous spectrum may be produced as primary colors (RGB) either concurrently or sequentially, for example, using a rotating filter wheel.

In systems according to the present invention, light sources to be used with the system of the invention and described in detail below are configured to provide continuous, uninterrupted illumination in the blue and green parts of the visible spectrum and discontinuous red and/or NIR light. The blue and green parts of the visible spectrum may be optically filtered from the emission produced by a continuous source or produced directly by a narrow-band source (e.g. blue and green LEDs). The red and NJR light may also be produced by an arc lamp, a halogen lamp, a solid state source (e.g., red and NIR LEDs or lasers), or any combination thereof.

Figure 2A:
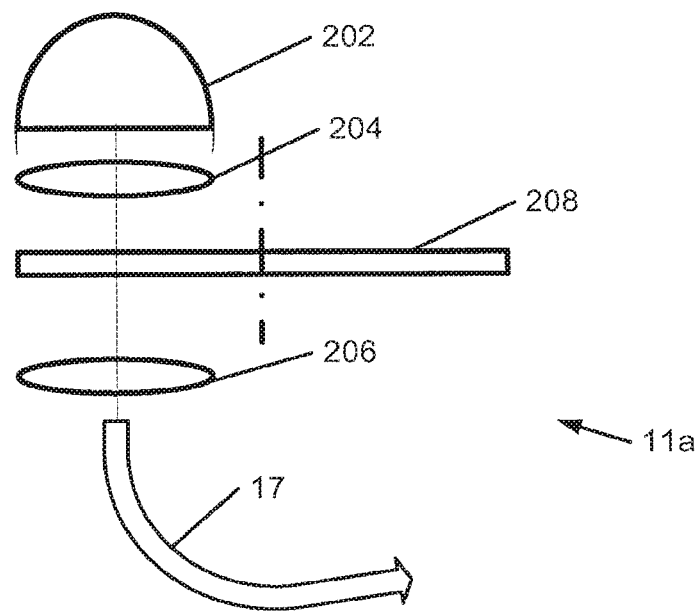
FIGS. 2a-2d show various exemplary embodiments of a multimode light source to be used with the endoscopic system of FIG. 1.

Turning now to FIG. 2a, in one embodiment a light source 11a includes an illuminator 202 producing visible and NIR light emission, a collimating lens 204, a filter wheel or reciprocating filter holder 208 that alternatingly transmits red and NIR light and continuously transmits green and blue light. Alternatively, a tunable electro-optic or acousto-optic filter may be used. The filtered light is focused by lens 206 onto light guide 17.

Figure 2B:
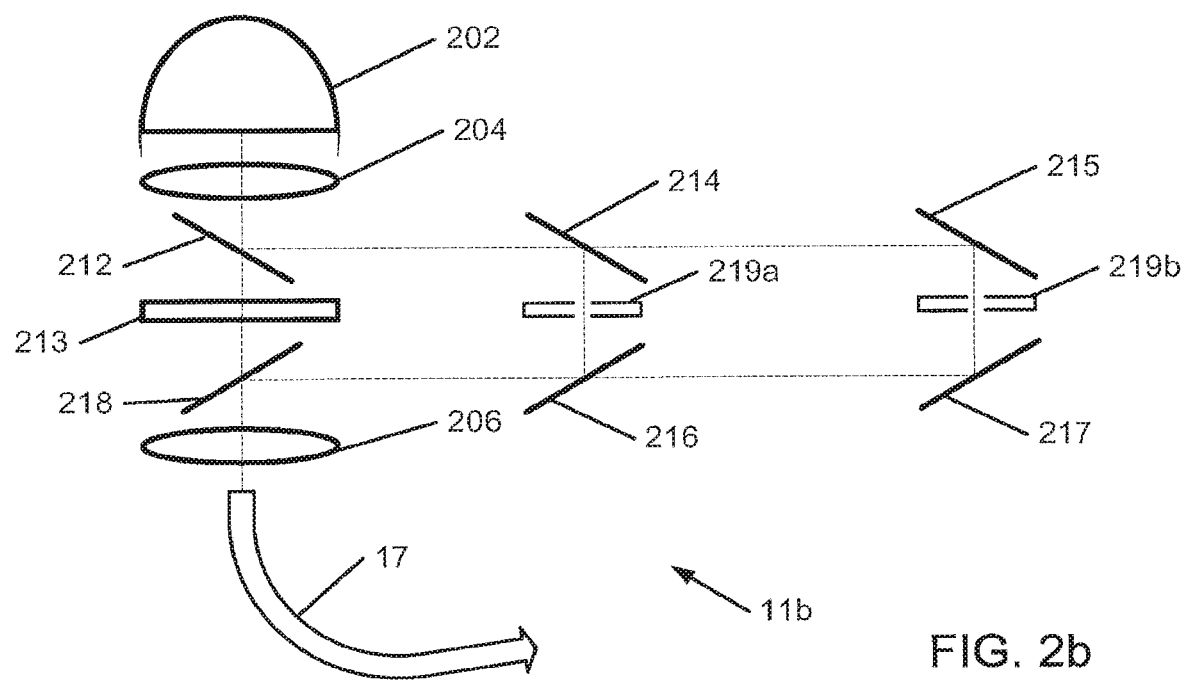

Another embodiment of a light source 11b is schematically illustrated in FIG. 2b. The light source 11b includes an illuminator 202 producing visible and NIR light emission and a collimating lens 204. A dichroic mirror 212 transmits green/blue light and reflects red/NIR light to another dichroic mirror 214 which transmits NIR light to NIR mirror 215 and reflects red light, or vice versa. The green/blue light can be further bandpass-filtered by filter 213. The reflected red and NIR light is chopped, for example, by chopper wheels 219a, 219b (which can be combined into a single chopper wheel) to produce temporally discontinuous illumination, which is then reflected by mirrors 216, 217 and combined with the green/blue light by dichroic mirror 218. The combined light is then focused by lens 206 onto light guide 17, as before.

Figure 2C:
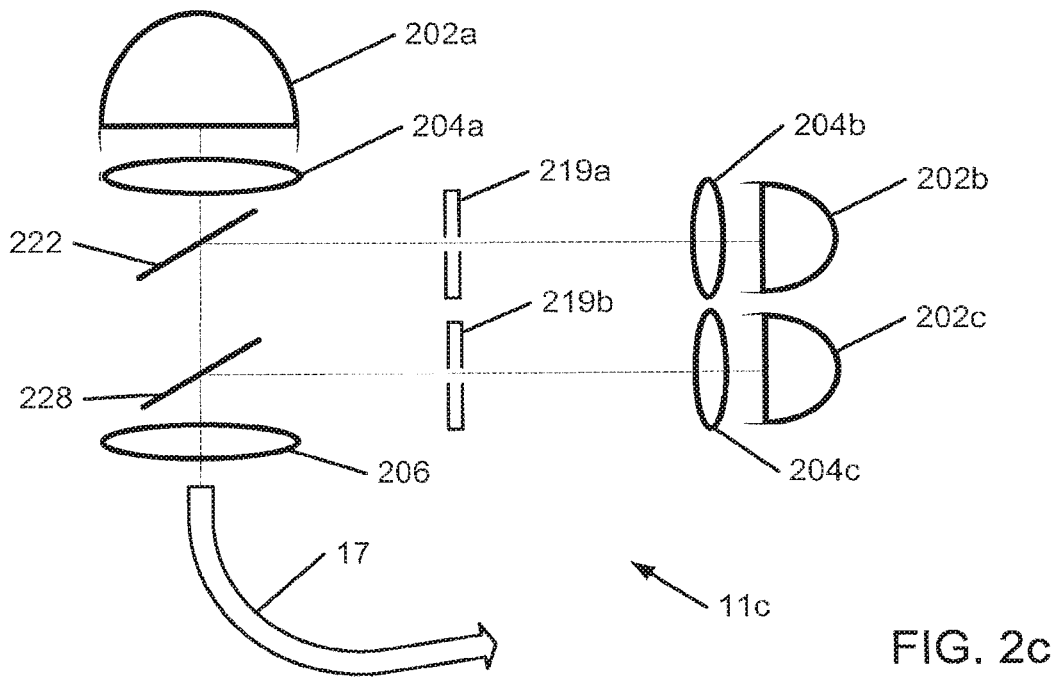

In another embodiment of a light source 11c schematically illustrated in FIG. 2c, an illuminator 202a produces green and blue light emission which is collimated by a collimating lens 204a. Likewise, separate illuminators 202b, 202c produce respective red and NIR light emissions which are collimated by corresponding collimating lenses 204b and 204c. As in the embodiment of FIG. 2b, the red and NIR light is chopped, for example, by chopper wheels 219a, 219b (which may also be combined into a single chopper wheel) to produce temporally discontinuous illumination, which is then combined with the green/blue illumination by dichroic mirrors 222, 228. The combined light is then focused by lens 206 onto light guide 17, as before.

Figure 2D:
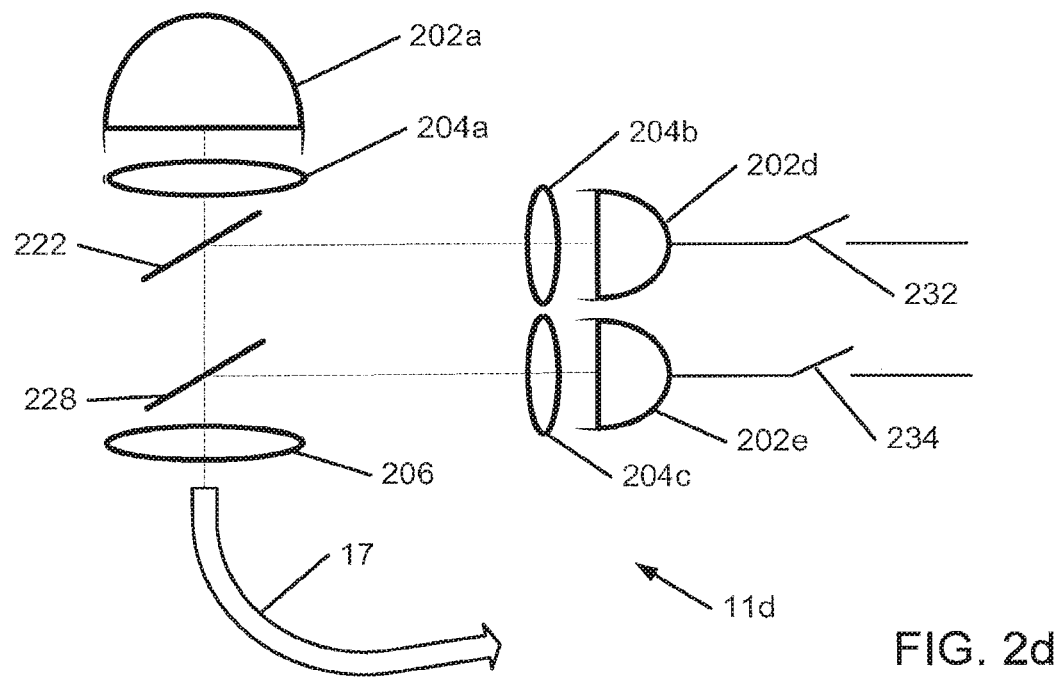

In yet another embodiment of a light source 11d schematically illustrated in FIG. 2d, an illuminator 202a produces green and blue light emission which is collimated by a collimating lens 204a, as before. However, unlike in the embodiment of FIG. 2c, the separate illuminators 202d, 202e are here switched electrically to produce red and NIR light emissions with controlled timing. For example, the red and NIR light sources 202d, 202e may be solid state light sources, such as LEDs or semiconductor lasers, which can be rapidly turned on and off with suitable, preferably electronic, switches. As described above with reference to FIG. 2c, the red and NIR illumination is collimated by corresponding collimating lenses 204b and 204c and combined with the green/blue illumination by dichroic mirrors 222, 228. The combined light is then focused by lens 206 onto light guide 17, as before.

The alternating red and NIR illumination is synchronized with the image acquisition of the three-sensor camera such that red and NIR images are acquired by the camera synchronously with the red and NIR illumination of the endoscope.

Figure 3A:
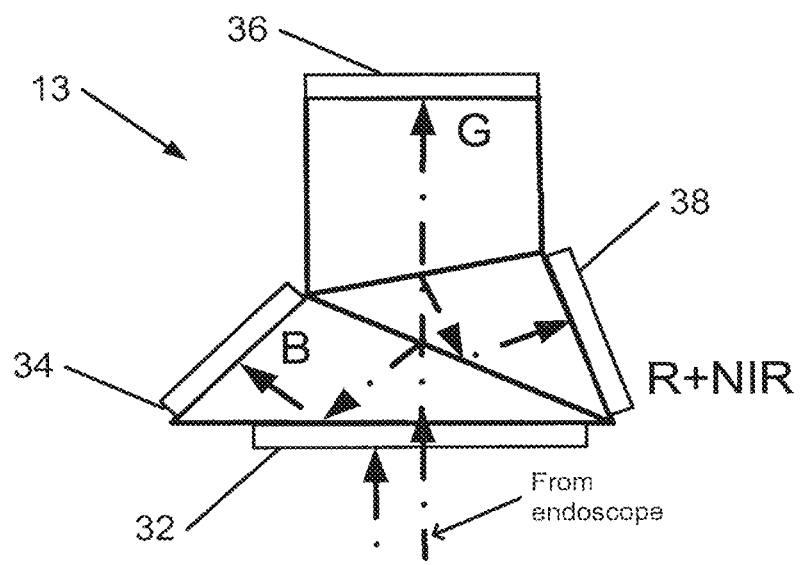
FIG. 3a shows an exemplary dichroic prism employed by a 3-sensor color camera.
Figure 3B:
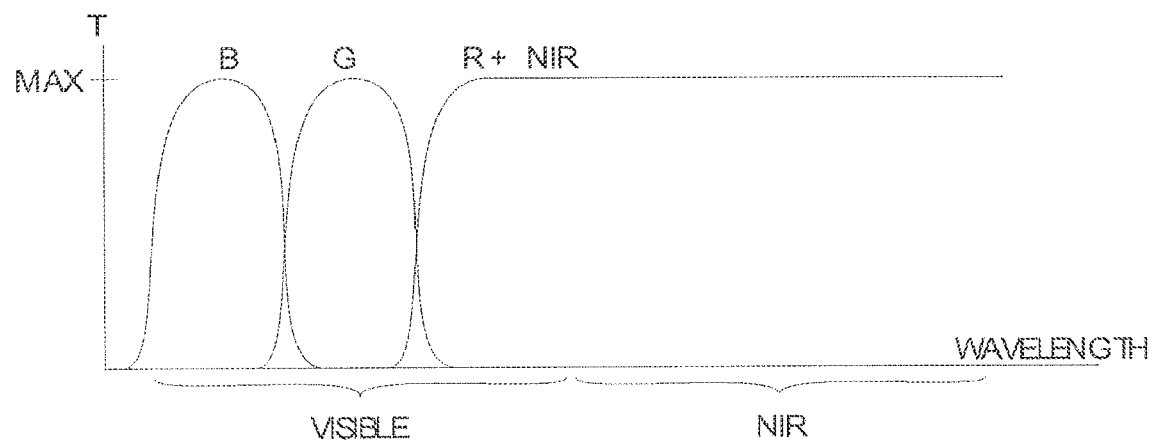
Figure 3C:
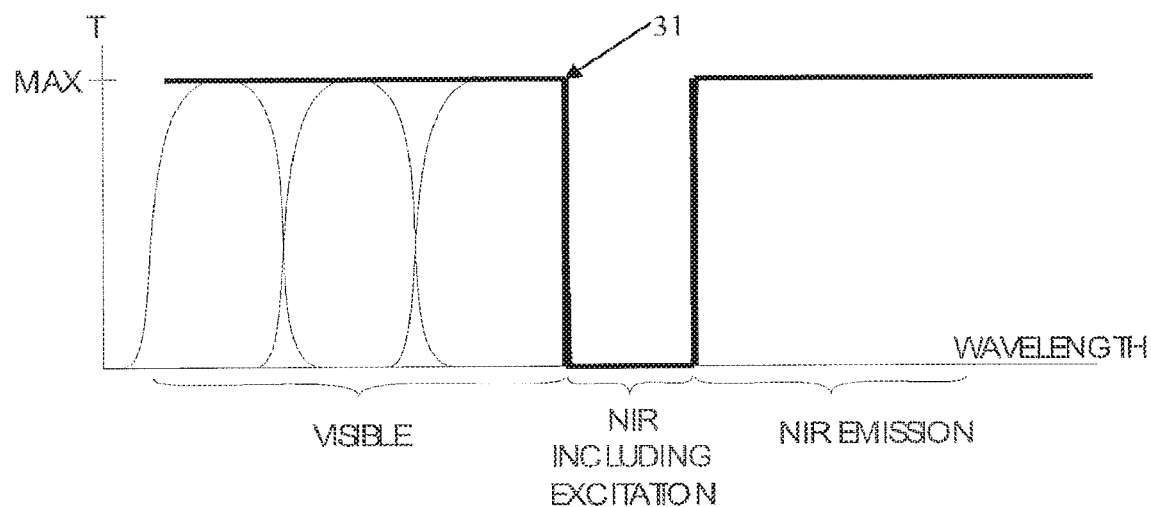
FIG. 3c shows the optical transmission range of a notch filter that blocks excitation light from entering the camera.

FIG. 3a shows in more detail the three-sensor camera 13 of FIG. 1, in particular the optical beam splitter used to direct red/NIR, green, and blue light to the three different image sensors 34, 36 and 38, respectively. For NIR fluorescence applications, the camera preferably also includes an excitation band blocking filter 32. The beam splitter may be made, for example, of a plurality of dichroic prisms, cube splitters, plate splitters or pellicle splitters. FIG. 3b shows the spectral composition of the light received from the endoscope according to FIG. 3a. FIG. 3c illustrates the spectral composition of the light transmitted through the excitation band blocking filter 32 implemented as a notch filter 31 which blocks transmission of excitation light, while transmitting the other wavelengths in the visible and NIR spectral range. The transmission characteristic of this filter 32 may be designed to also block undesired NIR wavelengths interfering with the visible spectrum that may degrade the color image.

FIG. 4 shows a timing diagram for a first exemplary embodiment of a simultaneous color and NIR imaging mode using, for example, a three-sensor camera. In this embodiment, the camera sensors utilize an interlaced read-out format which represents an advantageous combination of spatial and temporal resolution for smooth display of motion. Any of the light sources illustrated in FIGS. 2a-2d can be used with this embodiment. The light source provides continuous blue/green illumination and alternating red and NIR illumination. Half-frames are alternatingly exposed on the image sensors, i.e., a first field (half-frame) with even lines alternating with a second field (half-frame) with odd lines. In the timing diagram of FIG. 4 depicting a full frame rate of 30 fps, one field period (16.7 ms) provides NIR illumination, followed by two field periods (33.3 ms) of red illumination. Stated differently, the sample or tissue is illuminated with full-spectrum color (RGB) during two field periods (33.3 ms) and with GB and NIR during a third field period. For reconstructing the full-color visible image, the missing red information is interpolated between the fields adjacent to the field with the NIR illumination. The blue and green image information is always available, thereby providing optimum and continuous luma information. The NIR image is generated from every sixth field in each half frame, wherein the missing lines are spatially interpolated. When the fluorescence field is displayed, the image is updated every three fields, with the displayed image interpolated between even and odd lines.

In all the figures, the term "IR" is used instead of or interchangeably with "NIR."

Once the color and NIR image data have been processed, the signal is outputted to a video monitor and may be displayed as two separate, simultaneous views (one color and one fluorescence) or as combined color and fluorescence image signals (e.g. by assigning the fluorescence signal a color that contrasts with the naturally occurring colors in the tissue).

FIG. 5 shows a timing diagram for a second exemplary embodiment of a simultaneous color and NIR imaging mode. In this embodiment, the camera sensors utilize a progressive scan sensor read-out format wherein a complete frame (G/B/R alternating with G/B/NIR) is read out during each field period. Any of the light sources illustrated in FIGS. 2a-2d can be used with this embodiment. The light source provides continuous blue/green illumination and alternating red and NIR illumination. In the timing diagram of FIG. 5, one field period (16.7 ms) provides NIR illumination, followed by one field period (16.7 ms) of red illumination. Stated differently, the sample or tissue is illuminated with full-spectrum color (RGB) during one field period (16.7 ms) and with GB and NIR during a third field period. In this case, a full visible spectrum color image is available at every pixel, in every other frame. In the alternate frames, the blue and green information is acquired directly, whereas the red information is interpolated between adjacent frames. Unlike with the embodiment of FIG. 4, no spatial interpolation is required. Further image processing and display can be implemented in a manner similar to that described in previous embodiments.

FIG. 6 shows a timing diagram for a third exemplary embodiment, wherein both the green/blue illumination and the NIR illumination are continuous, while only the red illumination is modulated. Like in the embodiment of FIG. 4, half-frames are alternatingly exposed on the image sensors, i.e., a first field (half-frame) with even lines alternating with a second field (half-frame) with odd lines. In the timing diagram of FIG. 6 depicting a full frame rate of 30 fps, one field period (16.7 ms) provides (NIR+GB) illumination (red illumination switched off), followed by two field periods (33.3 ms) of (NIR+RGB). If the NIR image signal is small compared to the red reflected signal, it will not significantly affect the overall visible (RGB) image, so that the color image may be generated by conventional color image processing without correction. Otherwise the NIR contribution obtained in the red image channel when the red illumination is switched off may be subtracted from the (NIR+R) image data by spatial and temporal interpolation to obtain the red image signal, as shown in the second to last lien in the timing diagram of FIG. 6. Alternatively, sensors with a progressive scan image sensor readout similar to those illustrated in FIG. 5 could be used with RGB and (RGB+IR) image acquisition in alternate frames.

In yet another exemplary embodiment (not illustrated in the drawings), the green/blue illumination as well as the red illumination are continuous, whereas the NIR illumination is modulated. This timing scheme can be best applied if the red and NIR image signals have approximately the same magnitude. In this embodiment, the light source provides uninterrupted illumination with full visible spectrum and intermittent illumination with NIR light. The timing diagram is essentially the same as that depicted in FIG. 6, with the NIR and the red illumination interchanged. The intermittent NIR illumination is synchronized to coincide with every $3^{rd}$ field with interlaced cameras and with every other field in progressive scan cameras. For every field in which NIR illumination is provided, the red image sensor will acquire a (R+NIR) image signal. The NIR image signal can be extracted from the (R+NIR) image signal by interpolation of the red signal value from the appropriate preceding and subsequent "red only" image fields and subtracting the red image signal from the (R+NIR) signal. Since the red and NIR image signals are of similar magnitude, such interpolation and subtraction will provide a reasonably accurate NIR image signal value. The color image is processed by using the acquired and interpolated values for the red image signal in combination with the blue and green image signals. The resulting color and NIR image information can then be displayed or recorded as described before.

In any of the aforementioned embodiments, the NIR endoscopic imaging system can also be operated such that the light sources provides continuous illumination with either the full visible spectrum or the NIR spectrum and the camera acquires the corresponding color image or NIR (absorbance or fluorescence) image in a continuous fashion to provide high spatial resolution. The resulting video image of either individual illumination/imaging mode—color or NIR—can be subsequently displayed and/or recorded.

By implementing color and NIR imaging as described in the aforementioned embodiments, it is possible to acquire and display full-color visible light and NIR light images at video rates without compromising image resolution and/or introducing objectionable motion artifacts. Furthermore, should any residual color fringing occur as a consequence of sharp edges moving rapidly across the visual field (e.g. with the discontinuous acquisition of red or NIR images), these relatively minor effects can be mitigated by temporal interpolation of the missing (red/NIR) video fields with minimum additional processing time.

Figure 7:
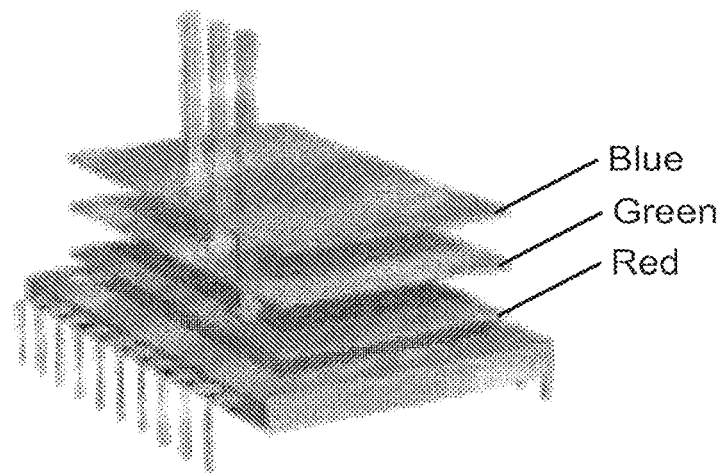
FIG. 7 shows an exemplary CMOS sensor having stacked imaging layers and the corresponding spectral sensitivity of these layers.
Figure 8:
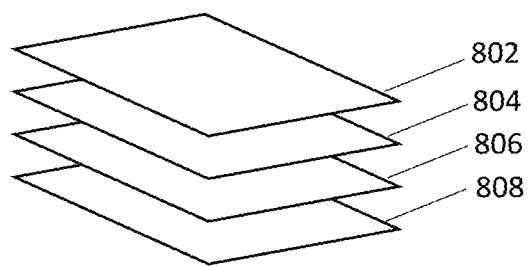
FIG. 8 shows four stacked imaging layers of an exemplary sensor.

While the invention has been disclosed in connection with the preferred embodiments shown and described in detail, various modifications and improvements thereon will become readily apparent to those skilled in the art. For example, instead of using separate image sensors for G/B and R/NIR, or a single color sensor for RGB images and NIR fluorescence images, a single direct three-color RGB sensor image sensor with a stacked pixel design implemented in CMOS technology and commercially available from Foveon, Inc., San Jose, Calif., may be used. Such sensor is schematically illustrated in FIG. 7. It will be understood that this sensor design can be extended to four colors by adding an NIR-sensitive layer. The red, green, blue and NIR images are hereby acquired at different depths in the image sensor. With a 4-layer sensor, such as a sensor having layers 802, 804, 806, 808 shown in FIG. 8, multiplexing of the red and NIR illumination would be unnecessary. However, with a 3-layer sensor, the red and NIR illumination would still need to be multiplexed, as described above for a 3-sensor conventional camera. An appropriate barrier filter to block the NIR excitation light would also be required for fluorescence imaging applications.

While the invention has been illustrated and described in connection with currently preferred embodiments shown and described in detail, it is not intended to be limited to the details shown since various modifications and structural changes may be made without departing in any way from the spirit and scope of the present invention. The embodiments were chosen and described in order to explain the principles of the invention and practical application to thereby enable a person skilled in the art to best utilize the invention and various embodiments with various modifications as are suited to the particular use contemplated.

What is claimed as new and desired to be protected by Letters Patent is set forth in the appended claims and includes equivalents of the elements recited therein:

What is claimed is:

1. A medical imaging system for acquisition of NIR images and full-color images comprising:
    a light source configured to provide visible light and NIR excitation light to a sample area; and
    a camera having an image sensor, the image sensor comprising:
        a barrier filter to block NIR excitation light, and
        sensor pixels arranged in a stacked array, the sensor pixels including:
            first sensor pixels located at a first depth in the image sensor, the first sensor pixels configured to detect blue reflectance light,
            second sensor pixels located at a second depth in the image sensor that is different from the first depth, the second sensor pixels configured to detect green reflectance light,
            third sensor pixels located at a third depth in the image sensor that is different from the first and second depths, the third sensor pixels configured to detect red reflectance light, and
            fourth sensor pixels located at a fourth depth in the image sensor that is different from the first, second, and third depths, the fourth sensor pixels configured to detect NIR fluorescence light received from the sample area.

2. The imaging system of claim 1, wherein the image sensor is a CMOS sensor.

3. The imaging system of claim 1, wherein the system is configured to generate NIR images and full-color images of the sample area.

4. The imaging system of claim 1, wherein the visible light provided by the light source comprises blue illumination light, green illumination light, and red illumination light, the blue illumination light being reflected from the tissue as blue reflectance light, the green illumination light being reflected from the tissue as green reflectance light, and the red illumination light being reflected from the tissue as red reflectance light.

5. The imaging system of claim 4, comprising a controller in signal communication with the light source and the camera, the controller being configured to:
    control the light source to illuminate the area under observation with the blue illumination light continuously and illuminate the area under observation with the red illumination light and the NIR illumination light, wherein at least one of the red illumination light and NIR illumination light is switched on and off periodically according to a predetermined timing scheme;
    simultaneously acquire a first image signal corresponding to the blue illumination light, and a second image signal corresponding to the red illumination light and the NIR illumination light; and
    determine the red reflectance light and detected NIR light from the second image signal, based on the predetermined timing scheme.

6. The imaging system of claim 5, wherein the predetermined timing scheme includes alternating the red illumination light and NIR illumination light.

7. The imaging system of claim 1, wherein the light source comprises an illuminator configured to emit a substantially constant intensity of visible light and NIR light over a continuous spectral range, and a plurality of filters disposed between the illuminator and the area under observation for transmitting temporally continuous blue light and temporally discontinuous red light and discontinuous NIR light.

8. The imaging system of claim 1, wherein the light source comprises one or more solid state sources.

9. The imaging system of claim 1, wherein the blue, green, and red illumination light are produced by blue, green, and red LEDs, respectively.

10. The imaging system of claim 1, wherein the imaging system is configured as an endoscope.

11. The imaging system of claim 1, wherein the NIR light detected by the camera is fluorescent light.

* * * * *